United States Patent
McKay et al.

(10) Patent No.: US 11,857,312 B2
(45) Date of Patent: Jan. 2, 2024

(54) HEARING ASSESSMENT SYSTEM AND METHOD

(71) Applicant: THE BIONICS INSTITUTE OF AUSTRALIA, East Melbourne (AU)

(72) Inventors: Colette McKay, East Melbourne (AU); Hamish Innes-Brown, East Melbourne (AU); Mehrnaz Shoushtarian, East Melbourne (AU); Stefan Weder, St. Brunswick (AU)

(73) Assignee: THE BIONICS INSTITUTE OF AUSTRALIA, East Melbourne (AU)

(*) Notice: Subject to any disclaimer, the term of this patent is extended or adjusted under 35 U.S.C. 154(b) by 727 days.

(21) Appl. No.: 16/630,173

(22) PCT Filed: Jul. 13, 2018

(86) PCT No.: PCT/AU2018/050726
§ 371 (c)(1),
(2) Date: Jan. 10, 2020

(87) PCT Pub. No.: WO2019/010540
PCT Pub. Date: Jan. 17, 2019

(65) Prior Publication Data
US 2020/0205699 A1    Jul. 2, 2020

(30) Foreign Application Priority Data

Jul. 13, 2017 (AU) ................................ 2017902753
May 9, 2018 (AU) ................................ 2018901572

(51) Int. Cl.
*A61B 5/12* (2006.01)
*A61B 5/00* (2006.01)
(Continued)

(52) U.S. Cl.
CPC ............ *A61B 5/125* (2013.01); *A61B 5/0075* (2013.01); *A61B 5/0205* (2013.01);
(Continued)

(58) Field of Classification Search
None
See application file for complete search history.

(56) References Cited

U.S. PATENT DOCUMENTS

| 4,007,731 A | 2/1977 | Griffiths et al. |
| 6,640,121 B1 | 10/2003 | Telischi et al. |
| 10,159,434 B1* | 12/2018 | Alla .................. A61B 5/14546 |

OTHER PUBLICATIONS

Pollonini; PHOEBE: a method for real time mapping of optodes-scalp coupling in functional near infrared spectroscopy; Biomedical Optics Express; published Nov. 15, 2016 (Year: 2016).*

(Continued)

*Primary Examiner* — Jay B Shah
(74) *Attorney, Agent, or Firm* — MARSHALL, GERSTEIN & BORUN LLP

(57) ABSTRACT

Embodiments generally relate to a method of assessing the hearing of a patient using functional near-infrared spectroscopy (fNIRS). The method comprises receiving at least one response signal from an optode placed on a scalp of the patient, the response signal comprising fNIRS data generated by the optode and relating to an aural stimulation received by the patient; comparing at least one parameter of the at least one response signal to a predetermined parameter value; and determining an auditory response of a patient based on the at least one parameter of the at least one response signal.

24 Claims, 19 Drawing Sheets

(51) Int. Cl.
*A61B 5/0205* (2006.01)
*A61B 5/1455* (2006.01)
*A61B 5/38* (2021.01)
*A61B 5/372* (2021.01)
*A61B 5/346* (2021.01)
*A61B 5/021* (2006.01)
*A61B 5/024* (2006.01)
*A61B 5/08* (2006.01)

(52) U.S. Cl.
CPC .......... *A61B 5/14553* (2013.01); *A61B 5/346* (2021.01); *A61B 5/372* (2021.01); *A61B 5/38* (2021.01); *A61B 5/6803* (2013.01); *A61B 5/6844* (2013.01); *A61B 5/7207* (2013.01); *A61B 5/7235* (2013.01); *A61B 5/7278* (2013.01); *A61B 5/021* (2013.01); *A61B 5/02416* (2013.01); *A61B 5/0816* (2013.01)

(56) References Cited

OTHER PUBLICATIONS

Hoppe et al.; Loudness perception and late auditory evoked potentials in adult cochlear implant users; Scand Audiol 2001;30:119-125 (Year: 2001).*
Bari et al., Study of neurovascular and autonomic response in a divided attention test by means of EEF, ECG and NIRS signals, Conf. Proc. IEEE Eng. Med. Biol. Soc., 2011:1403-6 (2011).
Bauernfeind et al., fNIRS for future use in auditory diagnostics, Current Directions in Biomedical Engineering, 2(1):229-32 (2016).
Delpy et al., Estimation of optical pathlength through tissue from direct time of flight measurement, Phys. Med. Biol., 33(12):1433-42 (Dec. 1988).
Ha et al., A wearable EEG-HEG-HRV multimodal system with real-time tES monitoring for mental health management, Solid-State Circuits Conference—(ISSCC) 2015, IEEE International, pp. 1-3, 22-26 (Feb. 2015).
Huppert et al., HomER: a review of time-series analysis methods for near-infrared spectroscopy of the brain, Appl. Opt., 48(10):D280-98 (Apr. 2009).
International Application No. PCT/AU2018/050726, International Preliminary Report on Patentability, dated Jan. 14, 2020.
International Application No. PCT/AU2018/050726, International Search Report and Written Opinion, dated Oct. 2, 2018.
Kamran et al., Cortical Signal Analysis and Advances in Functional Near-Infrared Spectroscopy Signal: A Review, Front Hum. Neurosci., 10:261 (Jun. 2016).
Molavi et al., Wavelet-based motion artifact removal for functional near-infrared spectroscopy, Physiol. Meas., 33(2):259-70 (Feb. 2012).
Oostenveld et al., The five percent electrode system for high-resolution EEG and ERP measurements, Clin. Neurophysiol., 112(4):713-9 (Apr. 2001).
Perdue et al., Extraction of heart rate from functional near-infrared spectroscopy in infants, J. Biomed. Opt., 19(6):067010 (Jun. 2014).
Pollonini et al., Auditory cortex activation to natural speech and simulated cochlear implant speech measured with functional near-infrared spectroscopy, Hear Res., 309:84-93 (Mar. 2014).
Rance et al., Hearing threshold estimation in infants using auditory steady-state responses, J. Am. Acad. Audiol., 16(5):291-300 (May 2005).
Sato et al., Reduction of global interference of scalp-hemodynamics in functional near-infrared spectroscopy using short distance probes, Neuroimage, 141:120-132 (Nov. 2016).
Visram et al., Cortical auditory evoked potentials as an objective measure of behavioral thresholds in cochlear implant users, Hear Res., 327:35-42 (Sep. 2015).
Von Luhmann et al., M3BA: A Mobile, Modular, Multimodal Biosignal Acquisition Architecture for Miniaturized EEG-NIRS-Based Hybrid BCI and Monitoring, IEEE Trans. Biomed. Eng., 64(6):1199-1210 (Jun. 2017).
Wiggins et al., Speech-evoked activation in adult temporal cortex measured using functional near-infrared spectroscopy (fNIRS): Are the measurements reliable?, Hear Res., 339:142-54 (Sep. 2016).

* cited by examiner

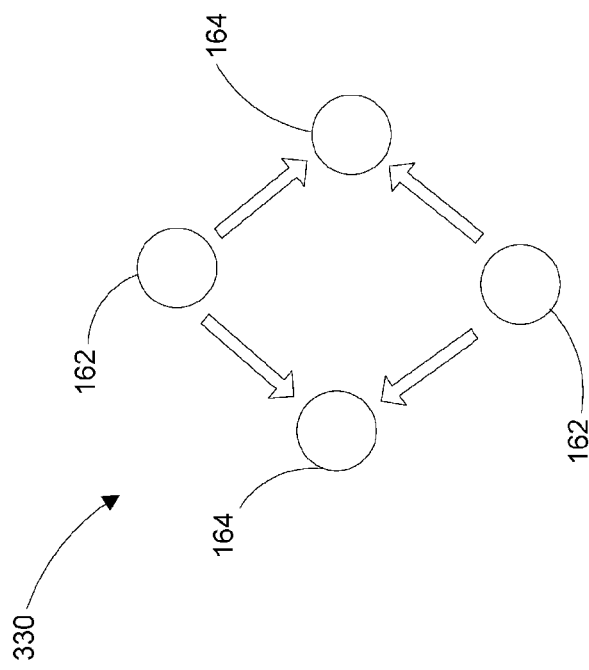
Figure 3c
Figure 3b
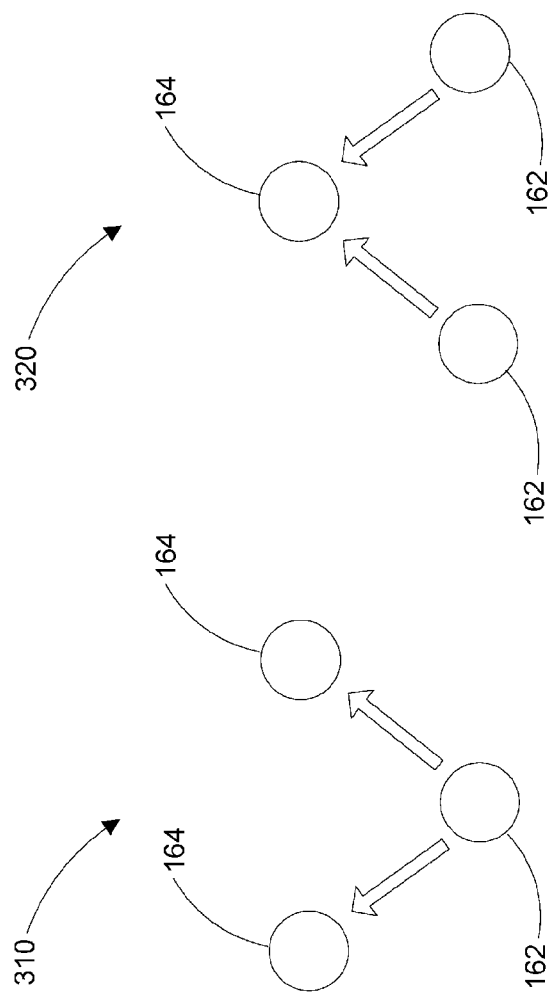
Figure 3a

HEARING ASSESSMENT SYSTEM AND METHOD

CROSS-REFERENCE TO RELATED APPLICATIONS

This application is a U.S. National Phase of International Application No. PCT/AU2018/050726 filed Jul. 13, 2017, which claims priority benefit under 35 USC § 119 of Australian Patent Application No. 2018901572, filed May 9, 2018, and Australian Patent Application No. 2017902753, filed on Jul. 13, 2017.

TECHNICAL FIELD

Embodiments generally relate to methods, devices and systems for hearing assessment. In particular, described embodiments are directed to methods, devices and systems for hearing assessment using measures of a patient's brain activity and/or cardiac activity.

BACKGROUND

Accurate assessment of hearing is important for screening and diagnosis of hearing impairment and also for validation of hearing instrument fitting. In the case of a hearing instrument, it is important to know whether the instrument has been adjusted so that an appropriate range of sound levels (such as those typical of speech) are audible and not too loud when the hearing instrument is worn.

Hearing assessments to determine the range of sound stimulus levels that elicit sound percepts in patients between thresholds of hearing and uncomfortably loud sounds are normally determined using behavioural tasks. For example, a patient may be asked to listen to a sound recording, and press on a button or otherwise give an indication of when they can hear a tone. By playing tones of various intensities, the patient's hearing range can be determined. However, some patients, such as infants, may find these tasks difficult, and so an objective hearing assessment is sometimes required.

Currently, electrophysiology may be used to measure the electrical activity of the brain stem or cortex in response to sounds. However, this method has limitations. For example, the auditory brainstem response or auditory steady-state response may not reflect true hearing thresholds of infants with auditory neuropathy spectrum disorder. Also, in sleeping infants, the electrical activity is suppressed. Furthermore, measuring the response with sounds routed through a hearing aid may not provide accurate information, and if the patient has a cochlear implant, electrical artefacts may interfere with the measurement.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

It is desired to address or ameliorate one or more shortcomings or disadvantages associated with prior systems for hearing assessment, or to at least provide a useful alternative thereto.

SUMMARY

Some embodiments relate to a method of assessing the hearing of a patient using functional near-infrared spectroscopy (fNIRS), the method comprising:
  receiving at least one response signal from an optode placed on a scalp of the patient, the response signal comprising fNIRS data generated by the optode and relating to an aural stimulation received by the patient;
  comparing at least one parameter of the at least one response signal to a predetermined parameter value; and
  determining an auditory response of a patient based on the at least one parameter of the at least one response signal.

According to some embodiments, the at least one response signal comprises signals relating to brain activity of the patient. According to some embodiments, the at least one response signal comprises signals relating to cardiac activity of the patient.

Some embodiments further comprise processing the at least one response signal to remove at least one unwanted signal element. In some embodiments, the at least one unwanted signal element comprises a signal element associated with at least one of the breathing of the patient, the heartbeat of the patient, a Mayer wave, a motion artefact, the brain activity of the patient, and measurement noise generated by a data collection apparatus.

In some embodiments, the at least one parameter includes a peak magnitude of the response signal. In some embodiments, the at least one parameter includes a width of the response signal. According to some embodiments, the at least one parameter includes a lag time of a peak magnitude of the response signal compared to the time at which the aural stimulation was received by the patient. In some embodiments, the at least one parameter includes values associated with modelling the response signal using an autoregressive integrative (ARI) model fit of the data.

According to some embodiments, the predetermined parameter value corresponds to a parameter of the aural stimulation received by the patient.

In some embodiments, the receiving at least one response signal comprises receiving a plurality of response signals, the method further comprising excluding any received response signals that are determined to be bad signals, wherein determining the auditory response of the patient comprises determining an auditory response based on at least one parameter derived from the remaining response signals. According to some embodiments, bad signals include signals that indicate poor coupling between the optode and the scalp.

Some embodiments further comprise filtering the at least one response signal. In some embodiments, filtering is performed using at least one of a low-pass filter, high-pass filter or a band-pass filter.

According to some embodiments, the receiving at least one response signal comprises receiving at least one signal from a first optode configured to measure brain activity of the patient and receiving at least one signal from a second optode configured to measure at least one signal that is not related to brain activity; the method further comprising producing a processed signal by removing at least one signal received from the second optode from at least one signal received from the first optode, to retain only information relating to brain activity from the at least one signal received from the first optode; wherein the determining an auditory response comprises determining an auditory response based on at least one parameter derived from the processed signal.

Some embodiments further comprise delivering the aural stimulation to the patient. Some embodiments further comprise the parameters of the aural stimulation delivered to the patient. According to some embodiments, the parameters of the aural stimulation are determined based on a measured auditory response signal based on previously delivered aural stimulation.

Some embodiments relate to a device for assessing the hearing of a patient using functional near-infrared spectroscopy (fNIRS), the device comprising:
  a processor;
  at least one data input channel;
    wherein the processor is configured to perform the method of some other embodiments, and wherein the response signal is received by the processor from the at least one data input channel.

Some embodiments further comprise memory accessible to the processor. Some embodiments further comprise a sound generation module to generate the aural stimulation received by the patient.

Some embodiments relate to a system for assessing the hearing of a patient using fNIRS, the system comprising:
  the device of some other embodiments; and
  a stimulation member to deliver the aural stimulation to the patient.

Some embodiments further comprise at least one source optode to emit NIR light, and at least one detector optode to measure light intensity and communicate data to the data input channel of the device corresponding to the light intensity.

According to some embodiments, the system comprises headgear configured to be worn by the patient and at least one source optode and the at least one detector optode are affixed to the headgear. In some embodiments, the source optodes and detector optodes are affixed to the headgear in a configuration such that when the headgear is correctly worn by the patient, the at least one source optode and the at least one detector optode are situated in the region of the temporal lobe of the patient.

Some embodiments further comprise a cardiac monitor configured to measure at least one form of cardiac data of the patient and to communicate data to the data input channel of the device. In some embodiments, the cardiac data comprises at least one of respiratory data, heartbeat data, and blood pressure data.

Some embodiments relate to a method of assessing the hearing of a patient using cardiac data, the method comprising:
  receiving at least one response signal derived from cardiac data collected from the patient, the at least one response signal relating to an aural stimulation received by the patient;
  comparing at least one parameter of a response signal to a predetermined parameter value; and
  determining an auditory response of a patient based on the at least one parameter of the at least one response signal.

According to some embodiments, the cardiac data comprises at least one of respiratory data, heartbeat data, and blood pressure data.

In some embodiments, the at least one parameter includes a peak magnitude of the response signal. In some embodiments, the at least one parameter includes a width of the response signal. In some embodiments, the at least one parameter includes a lag time of the response signal compared to the time at which the aural stimulation was received by the patient.

In some embodiments the at least one parameter includes a change in inter-peak intervals of the response signal. In some embodiments the at least one parameter includes a measure of reliability of a second parameter. In some embodiments the at least one parameter includes a measure of the magnitude of the auditory brainstem or cortical response potentials.

According to some embodiments, the predetermined parameter value corresponds to a parameter of the aural stimulation received by the patient.

Some embodiments further comprise delivering the aural stimulation to the patient. Some embodiments further comprise determining the parameters of the aural stimulation delivered to the patient. In some embodiments, the parameters of the aural stimulation are determined based on a measured auditory response signal based on previously delivered aural stimulation.

BRIEF DESCRIPTION OF DRAWINGS

Embodiments are described in further detail below, by way of example and with reference to the accompanying drawings, in which:

FIGS. 3a, 3b and 3c show example arrangements of optodes of the system of FIG. 1;

DETAILED DESCRIPTION

Described embodiments generally relate to methods, devices and systems for hearing assessment. In particular, described embodiments are directed to methods, devices and systems for hearing assessment using measures of a patient's brain activity and/or cardiac activity.

Figure 1:
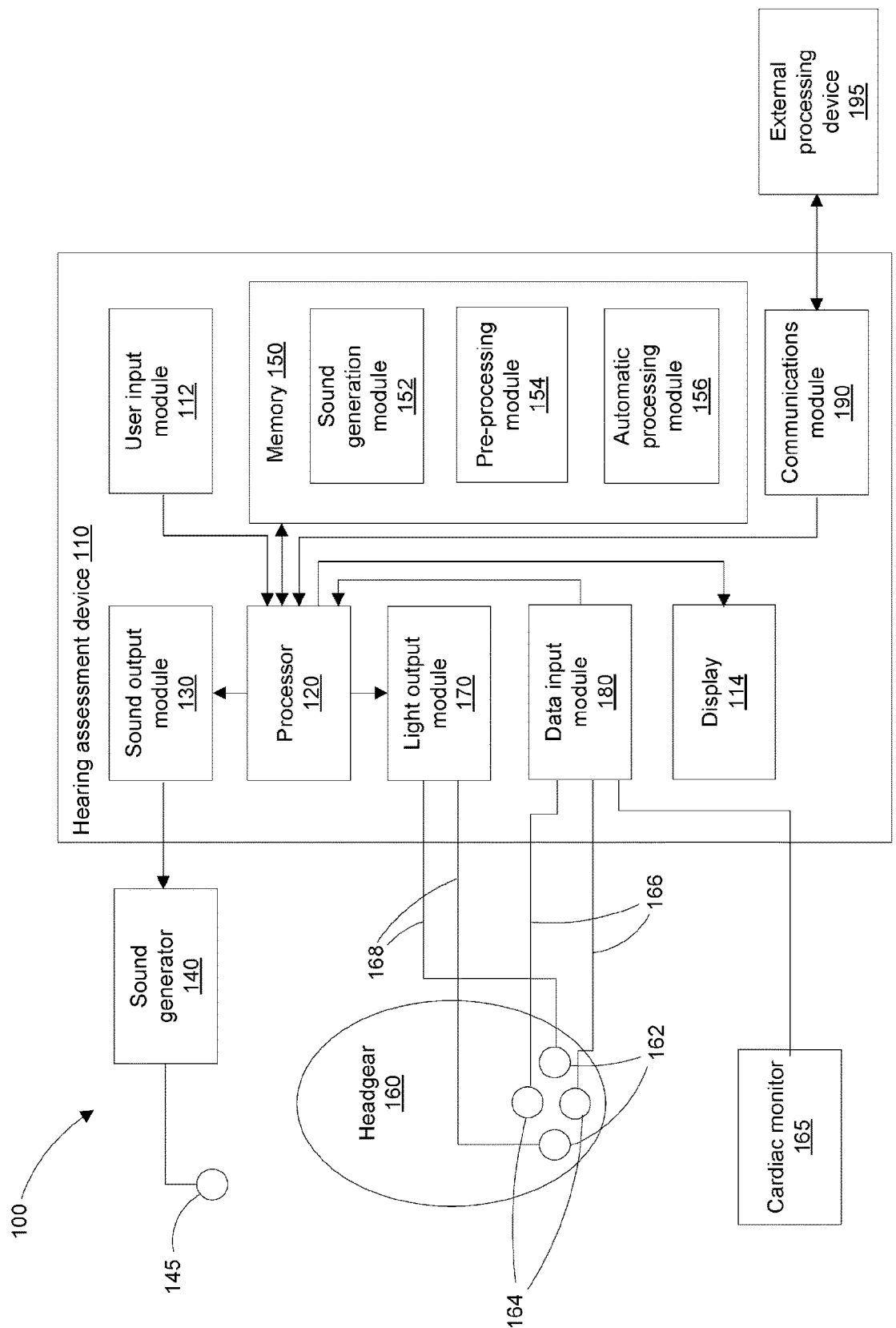
FIG. 1 shows a block diagram of a hearing assessment system according to some embodiments.

FIG. 1 shows a system 100 for hearing assessment using fNIRS. fNIRS is a brain imaging technique that uses light in the near-infrared spectrum to evaluate neural activity in the brain via changes in blood oxygenation. This is possible due to a range of wavelengths of near-infrared light over which skin, tissue, and bone are mostly transparent but in which blood is a stronger absorber of the light. Differences in the light absorption levels of oxygenated and deoxygenated blood allow the measurement of relative changes in blood oxygenation in response to brain activity.

fNIRS raw data measures changes in blood oxygenation, from which neural activity can be extracted using a series of processing steps. As well as neural activity, cardiac information signals can be extracted from the fNIRS raw data. fNIRS raw data is sensitive to cardiac information. Cardiac information in this context may include respiratory information, and may include information such as heart beat pulses, breathing and blood pressure changes. These cardiac information signals are often separated and rejected in fNIRS analyses, in order to avoid these additional signals from interfering with the measurement of relative changes in blood oxygenation in response to brain activity. According to some embodiments, system 100 may filter fNIRS data to remove cardiac information signals. According to some alternative embodiments, system 100 may use the cardiac information signals as additional or alternative sources of data for the hearing assessment.

System 100 is made up of a hearing assessment device 110, a sound generator 140, a stimulation member 145, and an external processing device 195. According to some embodiments, system 100 also comprises headgear 160. According to some embodiments, system 100 also comprises a cardiac monitor 165. According to some embodiments, system 100 may comprise only one of headgear 160 and cardiac monitor 165. According to some embodiments, system 100 may comprise both headgear 160 and cardiac monitor 165.

Hearing assessment device 110 has a processor 120, which communicates with a sound output module 130, memory 150, a light output module 170, a data input module 180 and a communications module 190. In the illustrated embodiment, sound generator 140 is a separate unit from assessment device 110. However, in some embodiments, sound generator 140 may be part of hearing assessment device 110.

Stimulation member 145 may be a speaker, earphone, hearing aid, hearing instrument, implantable auditory prosthesis comprising implantable electrodes, cochlear implant, brain stem implant, auditory midbrain implant, or other component used to provide aural stimulation to a patient. According to some embodiments, two stimulation members 145 may be used, to provide binaural stimulation. According to some embodiments, stimulation member 145 may be an audiometric insert earphone, such as the ER-3A insert earphone by E-A-RTONE™ 165 GOLD, US. In some embodiments, stimulation member 145 may interface with another component, such as a hearing aid or cochlear implant, in order to provide aural stimulation to the patient. Sound generator 140 causes the stimulation member 145 to produce a range of aural stimulation signals to assess the patient's hearing. When the patient has a cochlear implant, stimulation member 145 may be a computer and pod that interfaces directly with a coil of the cochlear implant, to cause the implant to produce electrical pulses that evoke sound sensations. In this case, sound generator 140 generates and transmits instructions for the patterns of electrical pulses to stimulation member 145.

Headgear 160 includes a number of optodes 162/164, having at least one source optode 162 and at least one detector optode 164. Source optodes 162 are configured to receive signals via transmission channels 168, and detector optodes 164 are configured to provide output signals via measurement channels 166. Headgear 160 may be a cap, headband, or other head piece suitable for holding optodes 162/164 in position on a patient's head. Optodes 162/164 may be arranged on headgear 160 to be positioned in the region of the auditory cortex of the patient when headgear 160 is worn correctly. In some cases, headgear 160 may have between 1 and 32 source optodes 162 and between 1 and 32 detector optodes 164. Source optodes 162 and their paired detector optodes 164 may be spaced at between 0.5 and 5 cm from one another on headgear 160. In some embodiments, headgear 160 may be an Easycap 32 channel standard EEG recording cap, and optodes 162/164 may be attached using rivets or grommets. According to some embodiments, headgear 160 may be an NIRScout system NIRScap by NIRX Medical technologies LLC, Germany. In some embodiments, headgear 160 may have 16 source optodes 162 and 16 detector optodes 164, making up to 256 channels or source-detector pairs.

Figure 7:
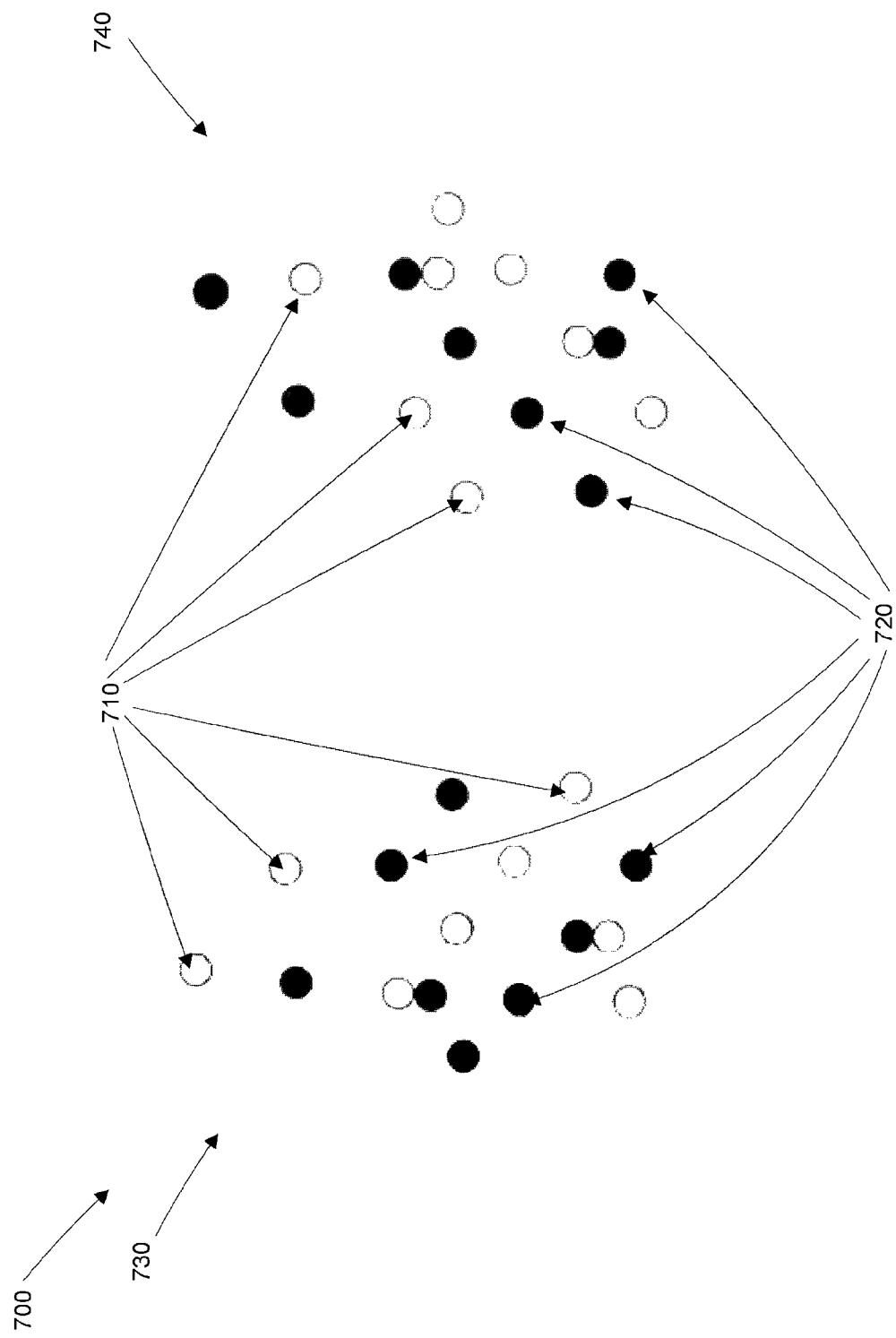
FIG. 7 shows a diagram of a patient's brain showing where optodes of the system of FIG. 1 may be positioned.

According to some embodiments, headgear 160 may be arranged so that source optodes 162 are arranged to be positioned in proximity to source positions 710 and detector positions 720 of a brain 700, as illustrated in FIG. 7, when headgear 160 is worn correctly on a patient's head. In FIG. 7, source positions 710 are illustrated in white, and detector positions 720 are illustrated in black. Headgear 160 may comprise sixteen source optodes 162 and sixteen detector optodes 164.

According to some embodiments, optodes 162/164 may be arranged to be positioned over at least one of the posterior temporal lobe, and the anterior temporal lobe/pre-frontal lobe of the patient's brain. Optodes 162 may be arranged to be positioned over either of the left hemisphere 730, the right hemisphere 740, or both hemispheres 730/740. According to some embodiments, source/detector pairs of source optodes 164 and detector optodes 164 may be located around 0.5 to 5 cm apart.

Figure 8:
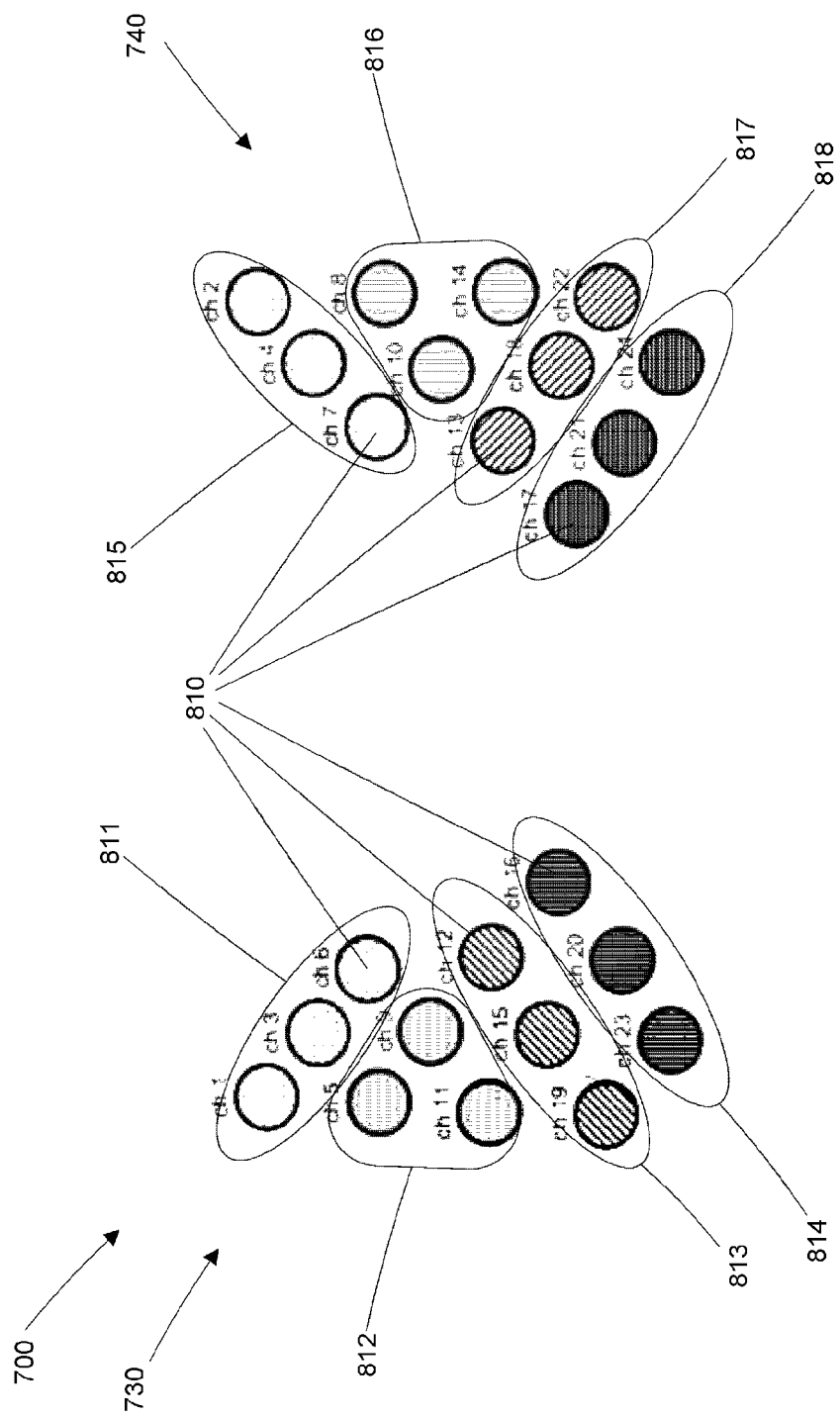
FIG. 8 shows the optodes of FIG. 7 grouped into regions of interest.

Optodes 162/164 as arranged in FIG. 7 allow for a number of different channels 810 of data to be obtained. According to some embodiments, twelve channels 810 of data are obtained from each hemisphere 730/740, being a total of 24 channels 810, as shown in FIG. 8. Each channel 810 comprises a source optode 162 and a detector optode 164, although each source optode 162 and detector optode 164 may belong to more than one channel 810, as described below with reference to FIG. 3. According to some embodiments, some of the channels 810 may be overlapping channels. Overlapping channels may allow for noise to be reduced from the data signals, by averaging the data from two overlapping channels. Furthermore, overlapping channels may be used as a backup for one another in case one of the channels stops working, or produces unacceptable data.

According to some embodiments, at least some optode source/detector pairs 162/164 may be arranged to operate as short channels, while some optode source/detector pairs 162/164 may be arranged to operate as long channels. Short channels may comprise pairs of optodes 162/164 located around 5 mm to 15 mm apart, and may be used to collect data from the scalp region only, which may include at least one signal that is not related to brain activity, such as cardiac signals, noise and other signals. According to some embodiments, short channels may comprise pairs of optodes 162/164 located around 11 mm apart. The short channels may be configured so as not to sense any brain activity. Long channels may be configured to be around 2 cm to 5 cm apart, and may be configured to sense brain activity as well as scalp activity. According to some embodiments, long channels may comprise pairs of optodes 162/164 located around 3 cm apart. Data received from the short channels may be removed from the data received by the long channels in order to separate the data related to brain activity from other signals, including cardiac data and noise. According to some embodiments, where only cardiac information is being used for a hearing assessment, all optodes 162/164 may be arranged to operate as short channels.

Channels 810 may be grouped into one or more regions of interest (ROIs). For example, as illustrated in FIG. 8, channels 810 may be divided into regions 811, 812, 813, 814, 815, 816, 817 and 818. Regions 811, 812, 813 and 814 may be located in the left hemisphere 730, while regions 815, 816, 817 and 818 may be located in the right hemisphere 740.

Regions 811 and 815 may comprise channels 810 located in the middle orbital gyrus, middle frontal gyrus and inferior frontal gyrus pars triangularis. Regions 812 and 816 may comprise channels 810 located in the inferior frontal gyrus pars orbitalis, inferior frontal gyrus pars operculatris, and superior temporal gyrus. Regions 813 and 817 may comprise channels 810 located in the precentral gyrus, Heschl's gyrus and middle temporal gyrus. Regions 814 and 818 may comprise channels 810 located in the postcentral cyrus, supramarginal gyrus and superior temporal gyrus.

According to some embodiments, headgear 160 may comprise a subset of optodes 162/164 as illustrated in FIG. 7. For example, in some embodiments headgear 160 may comprise optodes 162/164 located only in regions 811, 814, 815 and 818. As regions 812 and 813 are physically located between regions 811 and 814, and regions 816 and 817 are physically located between regions 815 and 818, the response in the 'middle' regions 812, 813, 816 and 817 is often a combination of the responses from the 'end' regions 811, 814, 815 and 818. As a result, measuring the response of 'middle' regions 812, 813, 816 and 817 may not produce any significant additional information that is not available from 'end' regions 811, 814, 815 and 818.

Referring again to system 100 of FIG. 1, cardiac monitor 165 may comprise one or more devices configured to measure cardiac information of a patient. The cardiac information may include heartbeat, respiration rhythm, systemic blood pressure and Mayer waves. Cardiac monitor 165 may comprise one or more of a heart rate monitor, a respiratory monitor, blood pressure monitor and Mayer wave monitor.

Although only one external processing device 195 is shown, assessment device 110 may be in communication with more than one external processing device 195, which may in some embodiments be desktop or laptop computers, mobile or handheld computing devices, servers, distributed server networks, or other processing devices. According to some embodiments, external processing device 195 may be running a data processing application such as Matlab 2016b (Mathworks, USA), for example. Filtering of received data signals may be done by external processing device 195 running Homer 2 functions in some embodiments.

Processor 120 may include one or more data processors for executing instructions, and may include one or more of a microprocessor, microcontroller-based platform, a suitable integrated circuit, and one or more application-specific integrated circuits (ASIC's).

Sound output module 130 is arranged to receive instructions from processor 120 and send signals to sound generator 140, causing sound generator 140 to provide signals to stimulation member 145. Where stimulation member 145 comprises a speaker or earphone, the signals may include an acoustic signal delivered via the earphone or speaker in the sound field. Where stimulation member 145 comprises a hearing instrument, the signals may comprise a digital sound file delivered via direct audio input to the hearing instrument. Where stimulation member 145 comprises an implantable auditory prostheses, the signals may comprise instructions for an electrical signal to be delivered by implanted electrodes in the implantable auditory prostheses.

Memory 150 may include one or more memory storage locations, either internal or external to optical read system 100, and may be in the form of ROM, RAM, flash or other memory types. Memory 150 is arranged to be accessible to processor 120, and contain program code that is executable by processor 120, in the form of executable code modules. These may include sound generation module 152, pre-processing module 154, and automatic processing module 156.

Light output module 170 is configured to receive instructions from processor 120 and send signals to source optodes 162 via transmission channels 168, causing source optodes 162 to generate near infra-red light. Data input module 180 is configured to receive data signals from detector optodes 164 via measurement channels 168, the data signals being generated based on the near infra-red light detected by detector optodes 164.

Communications module 190 may allow for wired or wireless communication between assessment device 110 and external processing device 195, and may utilise Wi-Fi, USB, Bluetooth, or other communications protocols.

User input module 112 may be configured to accept input from a number of user input sources, such as a touchscreen, keyboard, buttons, switches, electronic mice, and other user input controls. User input module 112 is arranged to send signals corresponding to the user input to processor 120. Display 114 may include one or more screens, which may be LCD or LED screen displays in some embodiments, and be caused to display data on the screens based on instructions received from processor 120. In some embodiments, assessment device 110 may further include lights, speakers, or other output devices configured to communicate information to a user.

System 100 may be used to determine the range of sound stimulus levels that elicit sound percepts in patients between their threshold of hearing and uncomfortably loud sounds. Control unit 120 may be configured to execute instructions read from sound generation module 152 of memory 150, to cause processor 120 to send instructions to sound output module 130. Sound output module may consequently communicate with sound generator 140, to cause sound generator 140 to generate a sound signal based on the instructions received. Sound generator 140 may output the sound signal to stimulation member 145 to cause stimulation member 145 to produce one or more sounds.

According to some embodiments, sound generator 140 may be configured to generate alternating periods of sounds and silence. Periods of sound may be 1 to 30 seconds in duration, and the periods of silence may be between 4 and 40 seconds in duration according to some embodiments. Sound generator 140 may be configured to generate sounds with varying levels of intensity or loudness. For example, the sounds may be adjustable within the dynamic range of the person being tested. For a person with normal hearing, the sounds may be adjustable between approximately 10 and 120 dB sound pressure level (SPL), for example. The characteristics of the sound (for example, band width, frequency, amplitude or frequency modulation) may be adjustable depending on the person being tested and the purpose of the testing. In some embodiments the alternating time periods may have sounds of different intensity or different type, instead of being periods of sounds and silence.

Figure 9:
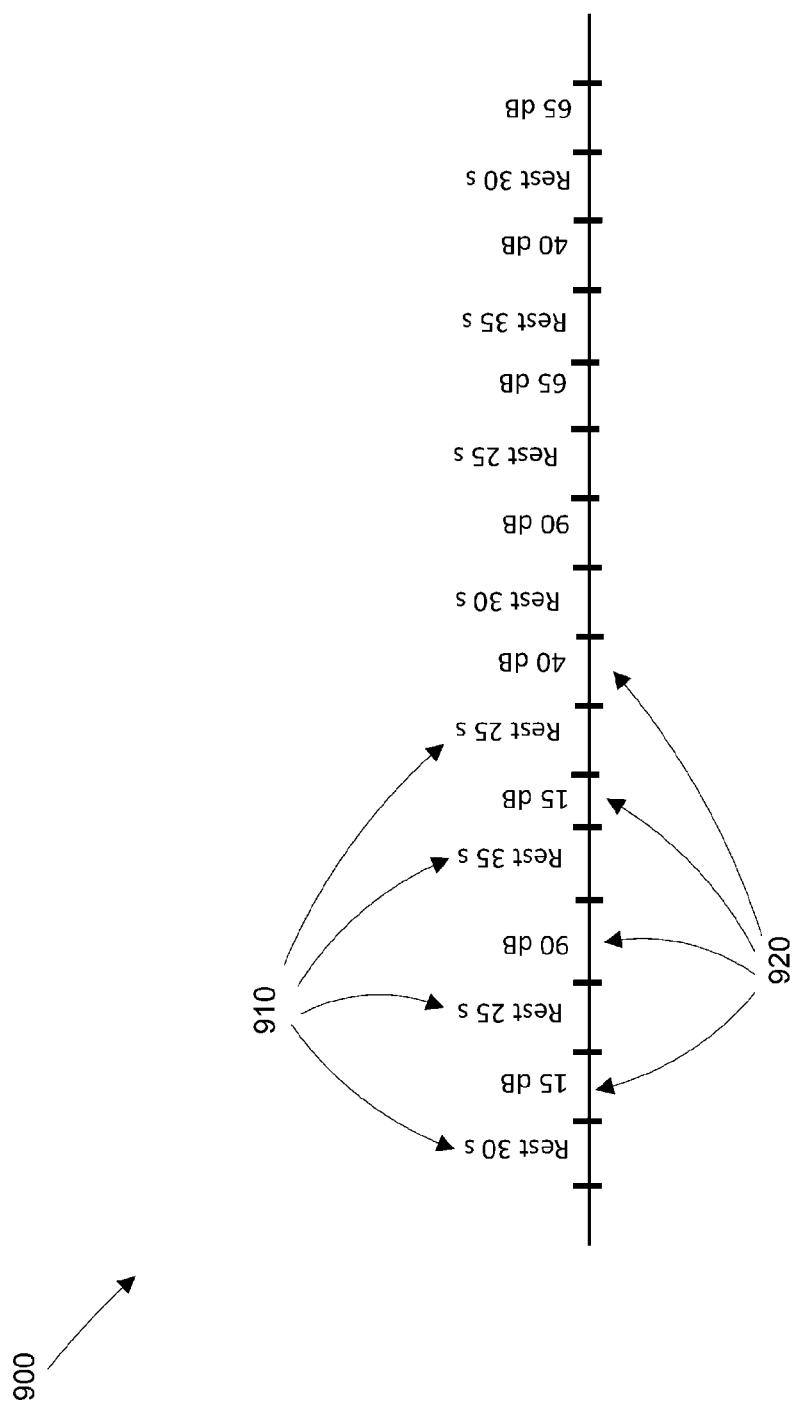
FIG. 9 shows an example series of sounds generated by sound generator of FIG. 1.

An example series of sounds generated by sound generator 140 is illustrated in FIG. 9, which shows the progression of example test period 900. According to some embodiments, a test session may include 1 or more test periods, such as 1, 2, 3, 4, 5, 6, 7, 8, 9, or 10 test periods, for example. Each test period may last for several minutes, such as between 5 and 10 minutes, for example. According to some embodiments, the test period may last for 7 minutes. According to some embodiments, 5 test periods of 7 minutes each may be carried out, so that the total test session may be around 35 minutes long.

Test period 900 includes eight blocks of rest 910. In the illustrated embodiment, each period of rest lasts for 25, 30 or 35 seconds, with the length of time applied at random. According to some embodiments, rest periods may last for between 5 and 180 seconds. In some embodiments, test periods may last between 20 and 40 seconds. According to some embodiments, test periods may last between 10 and 60 seconds. According to some embodiments, the test periods may be another suitable selected length of time.

Test period 900 further includes 8 stimulation periods 920, corresponding to times when stimulation would be delivered to a patient. According to some embodiments, each stimulation period 920 may last for between 1 and 30 seconds. For example, the stimulation period may last for 18 seconds in some embodiments. According to some embodiments, the length of each stimulation period 920 within a test period 900 may be equal. In the illustrated embodiment, a sound of 15 dB, 40 dB, 65 dB or 90 dB was played in each stimulation period 920, with the stimulation levels being applied at random. According to some embodiments, each stimulation level may be repeated a set number of times within a test period 900. For example, in the illustrated embodiment, each stimulation level is repeated twice within test period 900.

Stimulation member 145 may be positioned on or near a patient, in order to aurally stimulate the patient. Where headgear 160 is being used, headgear 160 may be positioned on the patient so that optodes 162/164 are positioned in proximity to the temporal lobe of the patient. Where cardiac monitor 165 is being used, cardiac monitor 165 may be positioned to measure cardiac information of the patient. When the patient hears a sound due to the stimulation provided by stimulation member 145, the neural activity in the patient's brain in the measured area, which may be at or around the auditory cortex, changes. According to some embodiments, the patient's heart rate, heart rate variability, blood pressure and/or breathing rate may also increase or decrease when the patient hears a sound. Optodes 162/164 are used to measure the changes in blood oxygenation in the auditory cortex region, which may be a result of changes in neural activity, and/or changes in heart rate, heart rate variability, blood pressure and/or breathing. Processor 120 sends instructions to light output module 170, which controls the light emitted by source optodes 162 by sending signals along transmission channels 168. This light passes through the measured region of the patient's brain, and some of the light is reflected back to detector optodes 164.

Data collected by detector optodes 164 is carried by measurement channels 166 to data input module 180, which communicates with processor 120. Cardiac monitor 165 may also be used to measure changes in heart rate, heart rate variability, blood pressure and/or breathing, and data signals collected by cardiac monitor 165 may also be carried by measurement channels to data input module 180, which communicates with processor 120. In some cases, the data may be stored in memory 150 for future processing by assessment device 110 or external computing device 195. In some embodiments, the data may be processed by assessment device 110 in real time. Processor 120 may execute pre-processing module 154 to pre-process the data as it is captured. Pre-processing module 154 may process the data by removing noise, and unwanted signal elements. According to some embodiments, these may include signal elements such as those caused by breathing of the patient, the heartbeat of the patient, a Mayer wave, a motion artefact, brain activity of the patient, and the data collection apparatus, such as measurement noise generated by the hardware. In some embodiments, the signal elements caused by breathing or heartbeats may be kept for further analysis, as described below. In some embodiments, pre-processing module 154 may pass the captured data through a low-pass filter to remove noise signals. In some embodiments, the filter may be a low-pass filter, such as a 0.1 Hz, 0.2 Hz, 0.3 Hz, 0.4 Hz, or 0.5 Hz low-pass filter, for example. In some embodiments, pre-processing module 154 may pass the captured data through a high-pass filter or a band-pass filter to remove noise signals. In some embodiments, the filter may be a high-pass filter, such as a 0.01 Hz, high-pass filter, for example. Pre-processing module 154 may additionally or alternatively use a transform to process the captured data, using a technique such as principle component analysis (PCA) for example. Pre-processing module 154 may transform the captured data to another domain, and then remove unwanted components of the data to retain only the desired data components. In some embodiments, pre-processing module 154 may model the response signal using an autoregressive integrative model fit of the data, as described in Barker et al. 2013 (Barker, Jeffrey W., Ardalan Aarabi, and Theodore J. Huppert. 'Autoregressive Model Based Algorithm for Correcting Motion and Serially Correlated Errors in FNIRS'. Biomedical Optics Express 4, no. 8 (1 Aug. 2013): 1366. https://doi.org/10.1364/BOE.4.001366), or a real-time implementation of an adaptive general linear model, as described in Abdelnour et al. 2009 (Abdelnour, A. Farras, and Theodore Huppert. 'Real-Time Imaging of Human Brain Function by near-Infrared Spectroscopy Using an Adaptive General Linear Model'. NeuroImage 46, no. 1 (15 May 2009): 133-43. https://doi.org/10.1016/j.neuroimage.2009.01.033). A method of pre-processing data that may be performed by pre-processing module 154 is described below with reference to FIG. 14.

As described in further detail below with reference to FIG. 6, processor 120 may subsequently execute automatic processing module 156, which may determine whether the aural stimulation provided by stimulation member 145 correlates to a change in activity in the auditory region as measured by the source-detector pair of optodes 162 and 164. This information may be determined by measuring the changes in attenuation of the light received by detector optode 164 compared to the light emitted by source optode 162. As described in further detail below with reference to FIG. 15, automatic processing module 156 may also determine whether the aural stimulation provided by stimulation member 145 was associated with a change in heart rate, heart rate variability, blood pressure, or breathing as measured by the source-detector pair of optodes 162 and 164. In some embodiments, automatic processing module 156 may also determine whether the aural stimulation provided by stimulation member 145 was associated with a change in heart rate, heart rate variability, blood pressure, or breathing as measured by the cardiac monitor 165.

Sounds generated by sound generator 140 may include sounds within the human hearing range. These may include pure tones in the range of 125 Hz to 16 kHz, for example. In some embodiments, frequency or amplitude modulated tones may be used. According to some embodiments, the sounds may include varying intensities of broadband modulated sound, with the intensities ranging from near-threshold to comfortably loud levels. According to some embodiments, four sound intensities may be used. For example, sounds may be played at 15 dB, 40 dB, 65 dB and 90 dB, according to some embodiments. Where the patient is an infant, band-passed infant-directed sounds may be used, such as infant-directed speech sounds. According to some embodiments, the sounds may include ICRA noise, as developed for the International Collegium of Rehabilitative Audiology. ICRA noise is a speech-like signal with long term average speech spectra and modulation characteristics like natural speech. Each sound may have a linear ramp of 10 ms applied at the start and end.

Source optodes 162 may generate near-infrared (NIR) light, being light having a wavelength of between 650 and 1000 nm. In some embodiments, light may be generated at two or more different frequencies, with one frequency being absorbed more by the oxygenated haemoglobin (HbO) in the blood than by non-oxygenated haemoglobin (HbR), and one frequency being absorbed more by HbR than by HbO. In such embodiments, one frequency of light may be chosen such that the wavelength of the light is below 810 nm, and the other may be chosen to have a wavelength of above 810 nm. For example, according to some embodiments, one frequency may be around 760 nm, and the other frequency may be around 850 nm. In this document, these wavelengths will be referred to as the first wavelength and the second wavelength, respectively.

Figure 2:
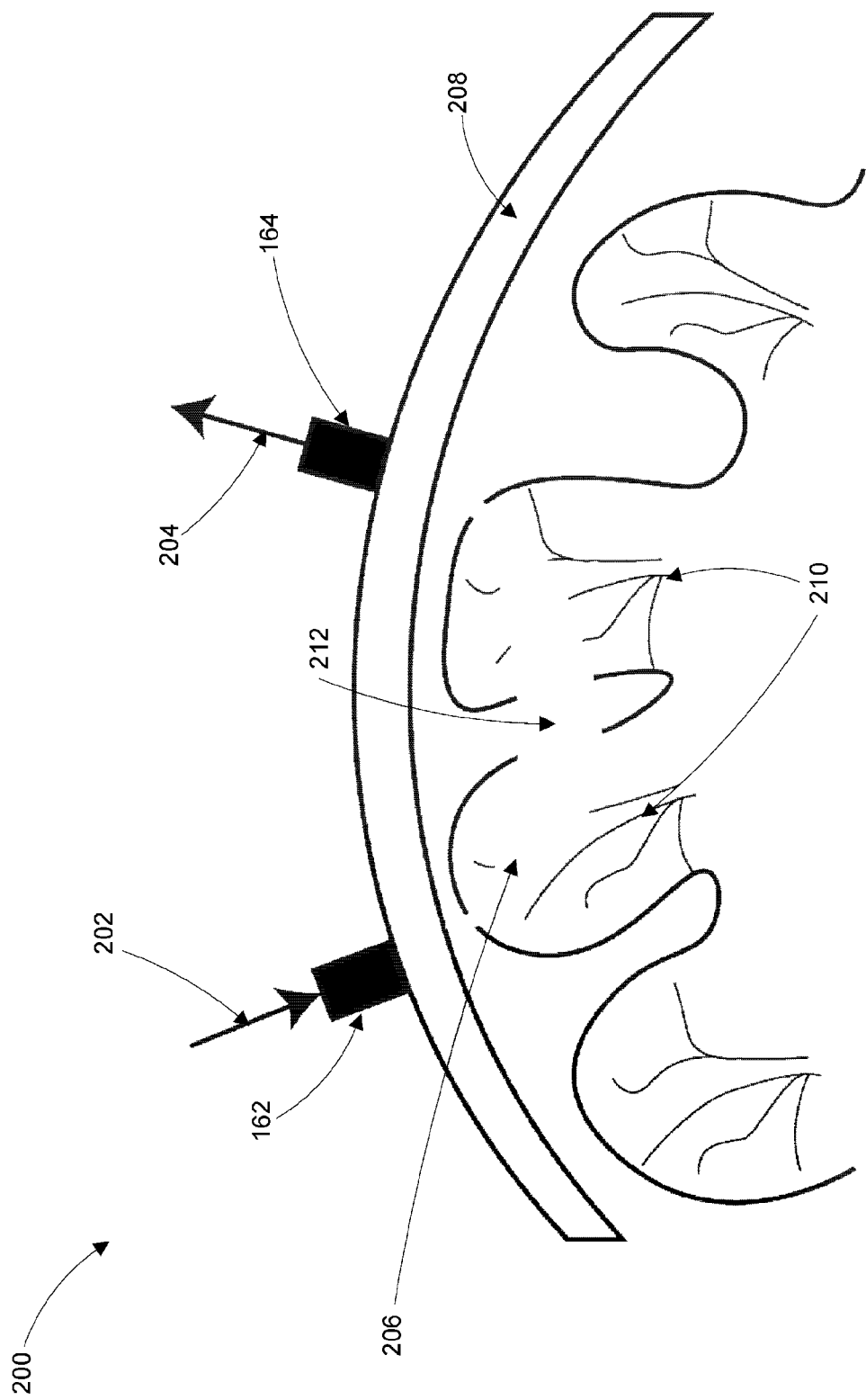
FIG. 2 shows a diagram of optodes from the system of FIG. 1 being used to perform hearing assessment on a patient.

FIG. 2 shows a diagram 200 of source optode 162 and detector optode 164 being used to perform fNIRS on a patient. fNIRS is an optical imaging technology that measures the light attenuation of the brain in a NIR spectrum, using light with a wavelength of around 650 to 1000 nm. Optodes 162 and 164 are placed on a scalp 208 of a patient, in the region of the temporal lobe tissue 206. Source 162 receives a signal 202 and emits NIR light into region 212. The NIR light passes through tissue 206 and is partially absorbed and partially reflected by blood vessels 210. The NIR light is mainly absorbed by the oxygenated haemoglobin (HbO) and the deoxygenated haemoglobin (HbR) in blood flow. The reflected light is captured by detector optode 164, and the data 204 is output, to be received by data input module 180. By measuring the change of light attenuation from a baseline state at two or more wavelengths, the changes of HbO and HbR concentrations (AHbO) and (AHbR) can be quantified. Haemodynamic changes in the brain have been demonstrated to be tightly coupled with changes in neuronal activations, as described in Logothetis N. K., Wandell B. A. (2004). "Interpreting the BOLD signal", Annu. Rev. Physiol. 66, 735-769 DOI:10.1146/annurev.physiol.66.082602.092845 [PubMed]. The raw signals and HbO and HbR also contain information about changes in heart rate, heart rate variability, blood pressure and breathing rate. A method 1500 of determining cardiac information is described below with reference to FIG. 15.

FIGS. 3*a* to 3*c* show various arrangements 310, 320 and 330 of optodes 162/164 showing how multiple data channels can be derived from each optode 162/164. Although particular arrangements are illustrated, it is envisaged that any arrangement of at least one source optode 162 and at least one detector optode 164 may be used.

FIG. 3*a* shows an arrangement 310 having one source optode 162, with two detector optodes 164. Light emitted by source optode 162 is captured by both detector optodes 164, giving data about two regions of the auditory cortex.

FIG. 3*b* shows an arrangement 320 having two source optodes 162, with one detector optodes 164. Light emitted by source optodes 162 is captured by detector optodes 164. By having each source optode 162 emit light sequentially or modulated at a different frequency, detector optode 164 can determine which source optode 162 the received data came from, and this arrangement therefore also allows for data about two regions of the auditory cortex to be captured.

FIG. 3*c* shows an arrangement 330 having two source optodes 162, with two detector optodes 164. Light emitted by each source optode 162 is captured by each detector optode 164. By having each source optode 162 emit light sequentially or modulated at a different frequency, each detector optode 164 can determine which source optode 162 the received data came from, and this arrangement therefore allows for data about four regions of the auditory cortex to be captured.

Figure 4:
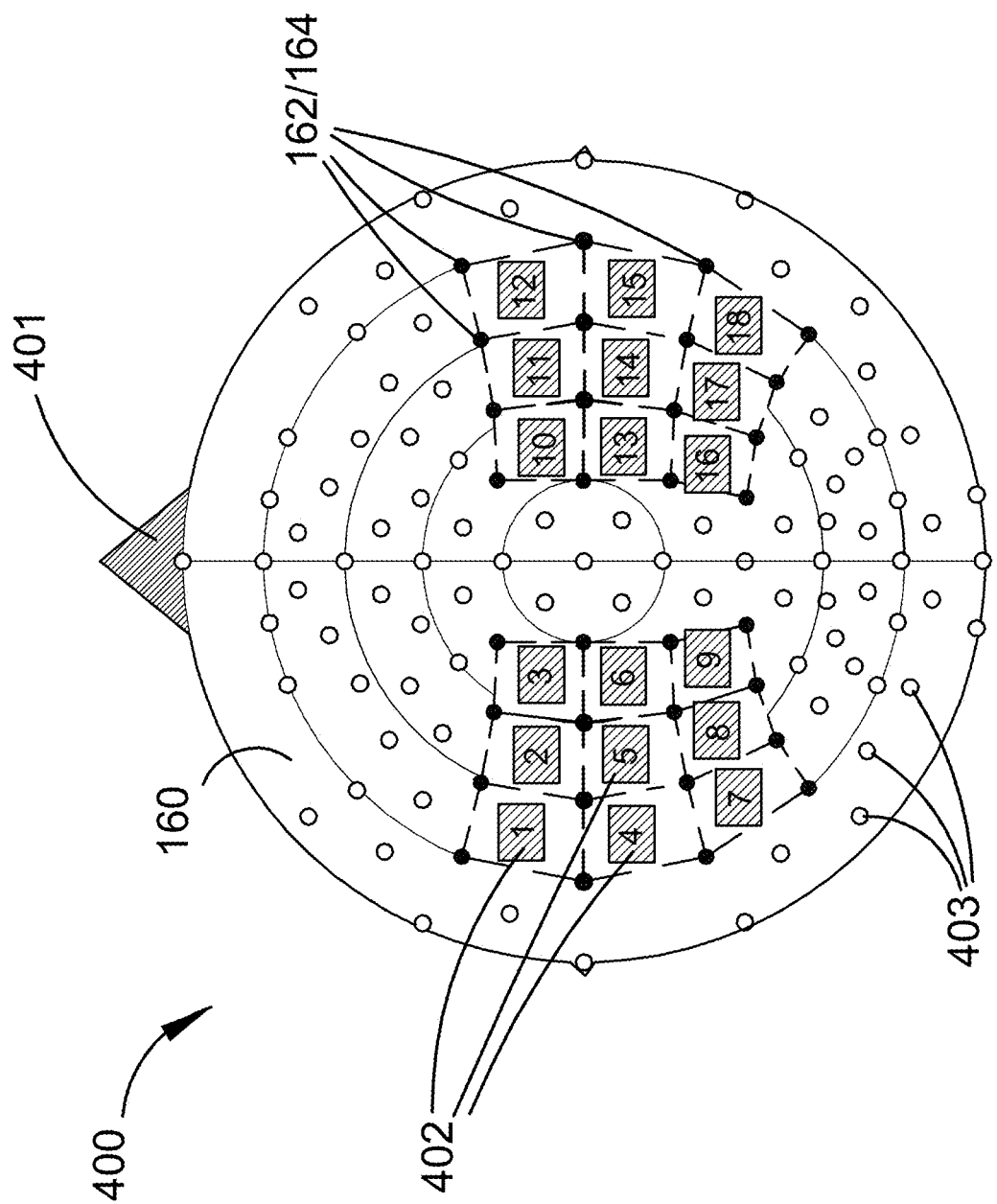
FIG. 4 shows a diagram of headgear of the system of FIG. 1 in position on a patient.

FIG. 4 shows a diagram 400 showing headgear 160 in position on a patient 401, where headgear 160 is an elastic cap with optodes positioned according to standard 10-5 system locations as described in Oostenveld R & Praamstra P (2001), "The five percent electrode system for high-resolution EEG and ERP measurements", Clinical neurophysiology: official journal of the International Federation of Clinical Neurophysiology 112(4):713-719. 18 regions of interest 402 are labelled, showing where 32 optodes 162/164 may be placed. Areas 403 show other areas of the 10-5 system cap where optodes 162/164 may be placed, but which are empty in the illustrated arrangement. FIGS. 7 and 8, as described above, show an alternative arrangement of optodes 162/164 on a brain 700 of a patient 401. According to some embodiments, at least some of optodes 162/164 may be located over the temporal lobe region of the patient.

Figure 5:
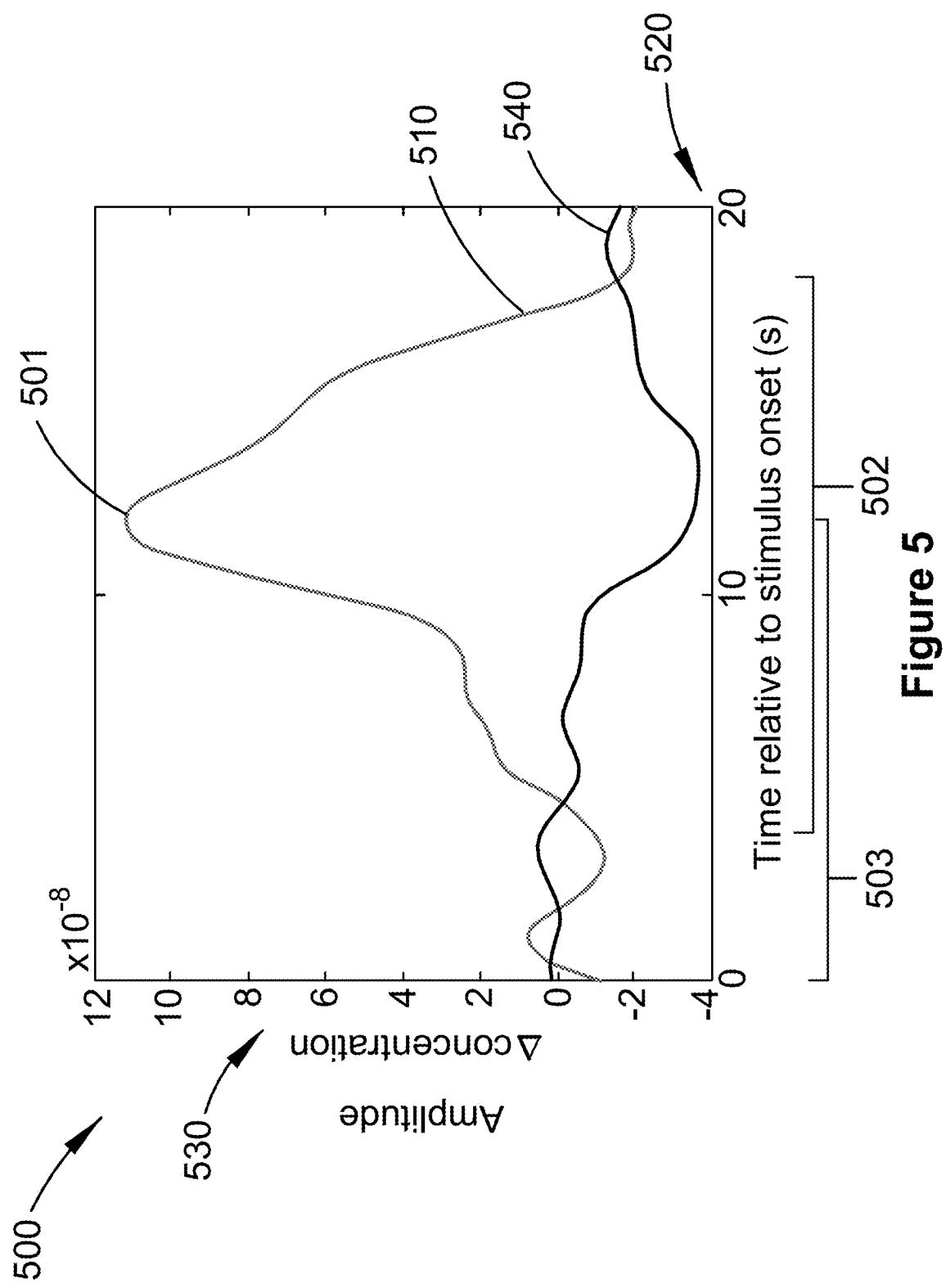
FIG. 5 shows an example response signal that may be measured by optodes of the system of FIG. 1.

FIG. 5 shows an example graph 500 of response signals 510 and 540 received from a detector optode 164 situated in a left hand auditory cortex area of a patient 401 when auditory stimulation was administered to patient 401. Axis 520 shows the time scale in seconds, while axis 530 shows the amplitude of the response as a change in concentration of HbO or HbR. Response signal 510 shows the change in the concentration of HbO over time, and has a number of key features, including a peak magnitude 501, a width 502, and a time-to-peak (or lag time of the peak magnitude) 503 measured from the time the auditory stimulation was started. According to some embodiments, key features may also include values associated with modelling the response signal using an autoregressive integrative (ARI) model fit of the data, changes in inter-peak intervals of the signal, measures of reliability of parameters of the signal, measures of the magnitude of the auditory brainstem or cortical response potentials, or beta-values obtained from modelling the response signal using a general linear model. These key features may be derived by a method such as that described in Picton T W "Human auditory evoked potentials" Plural Publishing inc, San Diego, 2011; Rance et al. "Hearing threshold estimation in infants using auditory steady-state responses" J Am Ac Audiol, 2005, 16:291-300; or Visram et al "Cortical auditory evoked potentials as an objective measure of behavioral thresholds in cochlear implant users," Hear Res, 2015, 327: 35-42.

Response signal 540 shows the change in the concentration of HbR over time. In the illustrated example, the auditory stimulation was provided at time=0. FIGS. 10A to 12, described in further detail below, show alternative graphs of response signals obtained via system 100.

Figure 6:
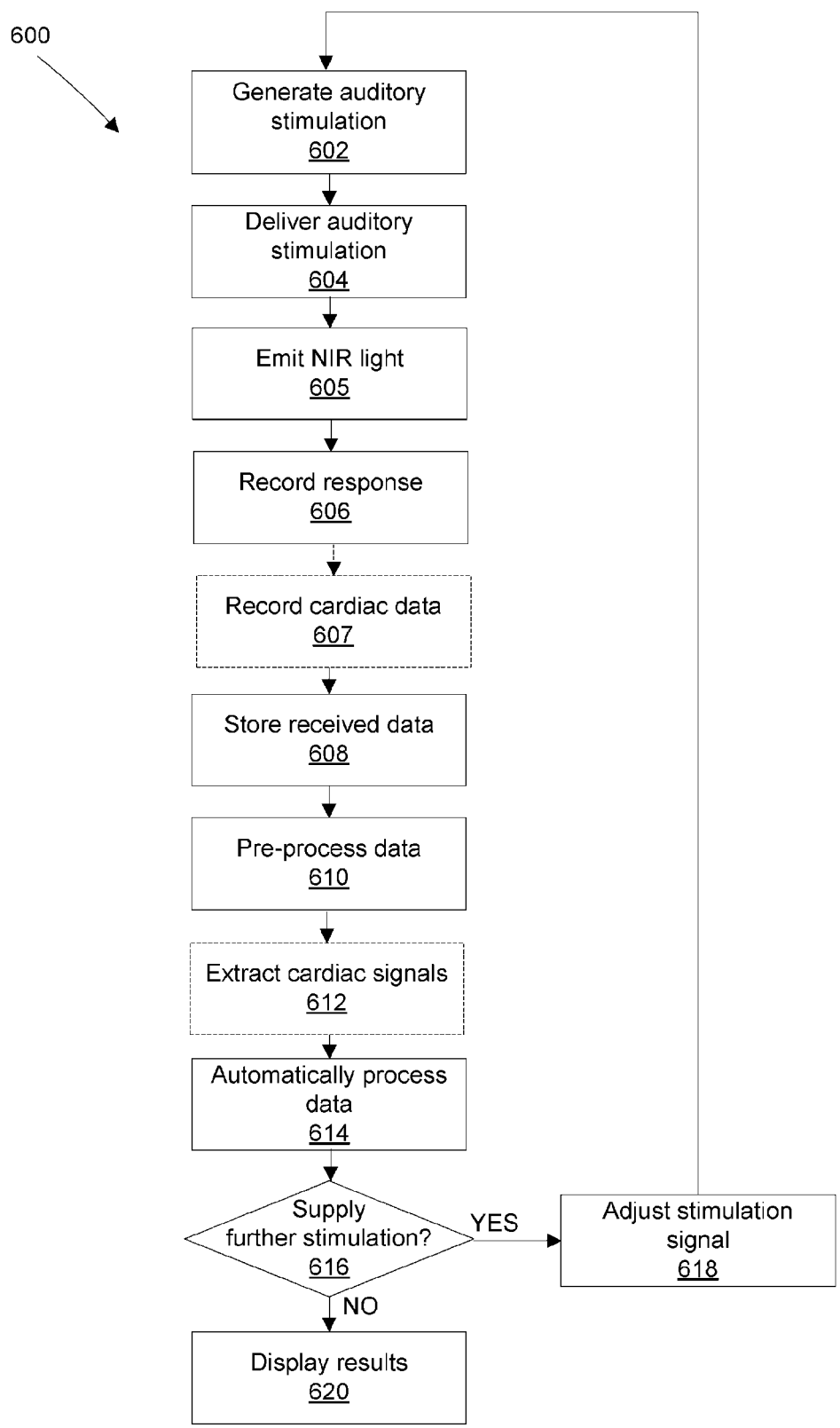
FIG. 6 shows a flow diagram illustrating an example method using the system of FIG. 1.

FIG. 6 shows a flow diagram 600 illustrating a method of assessing the hearing of a patient using system 100. At step 602, processor 120 may execute sound generation module 152, causing processor 120 to instruct sound output module 130 to generate an auditory stimulation signal having parameters as determined by sound generation module 152. This step may be initiated based on an input signal received by user input module 112 and communicated to processor 120. Parameters of the stimulation may be supplied, such as the frequency and duration of the stimulation, are stored in memory 150. According to some embodiments, the parameters of the stimulation may be pseudo-randomly determined as described above with reference to FIG. 1.

In some alternative embodiments, sound generator 140 may determine the stimulation parameters, rather than receiving them from assessment device 110. In these embodiments, sound generator 140 may communicate the parameters of stimulation to device 110.

At step 604, sound generator 140 may receive instructions from sound output module 130, and cause stimulation member 145 to deliver an auditory stimulation signal. This may be in the form of a sound, where stimulation member 145 is a speaker or headphone, or it may be in the form of an electrical signal, where stimulation member 145 is an interface to a cochlear implant, for example.

At step 605, processor 120 instructs light output module 170 to cause source optodes 162 to emit NIR light. In some embodiments, light output module 170 may cause source optodes 162 to emit NIR light continuously, independent of stimulation provided by stimulation member 145. At step 606, detector optodes 164 record the intensity of any NIR light received, and transmit the data to data input module 180 via measurement channels 166.

In some embodiments, method 600 may include step 607. Step 607 may involve cardiac monitor 165 generating data signals related to cardiac information of the patient, and transmitting the data to data input module 180.

At step 608, data received by data input module 180 is stored by processor 120 in memory 150. In some embodiments, at this point, the data may also or alternatively be transmitted to external processing device 195 for storage and/or processing.

In the illustrated embodiment, at step 610 processor executes pre-processing module 154. According to some embodiments, pre-processing module 154 may perform a pre-processing method such as method 1400, described below with reference to FIG. 14. In some embodiments, pre-processing module 154 checks that data is being received, and instructs processor 120 to cause a warning or alert to be displayed on display 114 if no data signals or data signals of poor quality are detected. This may indicate that optodes 162/164 or cardiac monitor 165 are faulty, for example, or are incorrectly positioned. Pre-processing module 154 may also exclude data received from channels 810 that lack a predetermined degree of correlation between the signals in the first wavelength and the second wavelength. For example, according to some embodiments signals with a correlation of less than 0.75 may be discarded. In other embodiments, channels 810 may be discarded based on the detected light intensity being too high or too low (which may indicate poor optode/skin contact).

Pre-processing module 154 may also process the incoming data signals received from data input module 180 to extract just the data relating to rates of change of HbO and HbR that are due to changes in brain activity, and to remove unwanted aspects of the signal, such as drift, broadband noise, motion artefacts, and signals dues to heartbeat and respiration. The unwanted aspects of the incoming data signals may be removed by wavelet analysis and/or by applying one or more bandpass filters. According to some embodiments, bandpass filters of 0.01 and 0.5 Hz may be applied. According to some embodiments, the rates of change of HbO and HbR may be estimated by applying the modified Beer Lambert Law. According to some embodiments, unwanted aspects of the signal may also be removed by subtracting short channel data from long channel data, as described below with reference to step 1412 of FIG. 14.

In some embodiments, pre-processing module 154 may model the response signal using an autoregressive integrative model fit of the data as described in Barker et al. 2013, or a real-time implementation of an adaptive general linear model as described in Abdelnour et al. 2009, as described below with reference to step 1426 of FIG. 14. In some embodiments, method 600 may include step 612. At step 612, cardiac signals may also be extracted from the incoming data signals received from data input module 180. The cardiac signals may include signals relating to changes in heart rate, heart rate variability, blood pressure and/or breathing of the patient. The cardiac signals may be extracted from fNIRS data generated by channels 810, or from data generated by cardiac monitor 165. According to some embodiments, a cardiac information processing method such as method 1500 may be performed. Method 1500 is described in further detail below with reference to FIG. 15.

According to some embodiments, step 610 may be performed at the same time or in parallel to step 612. According to some embodiments, step 612 may be performed before step 610.

Figure 12:
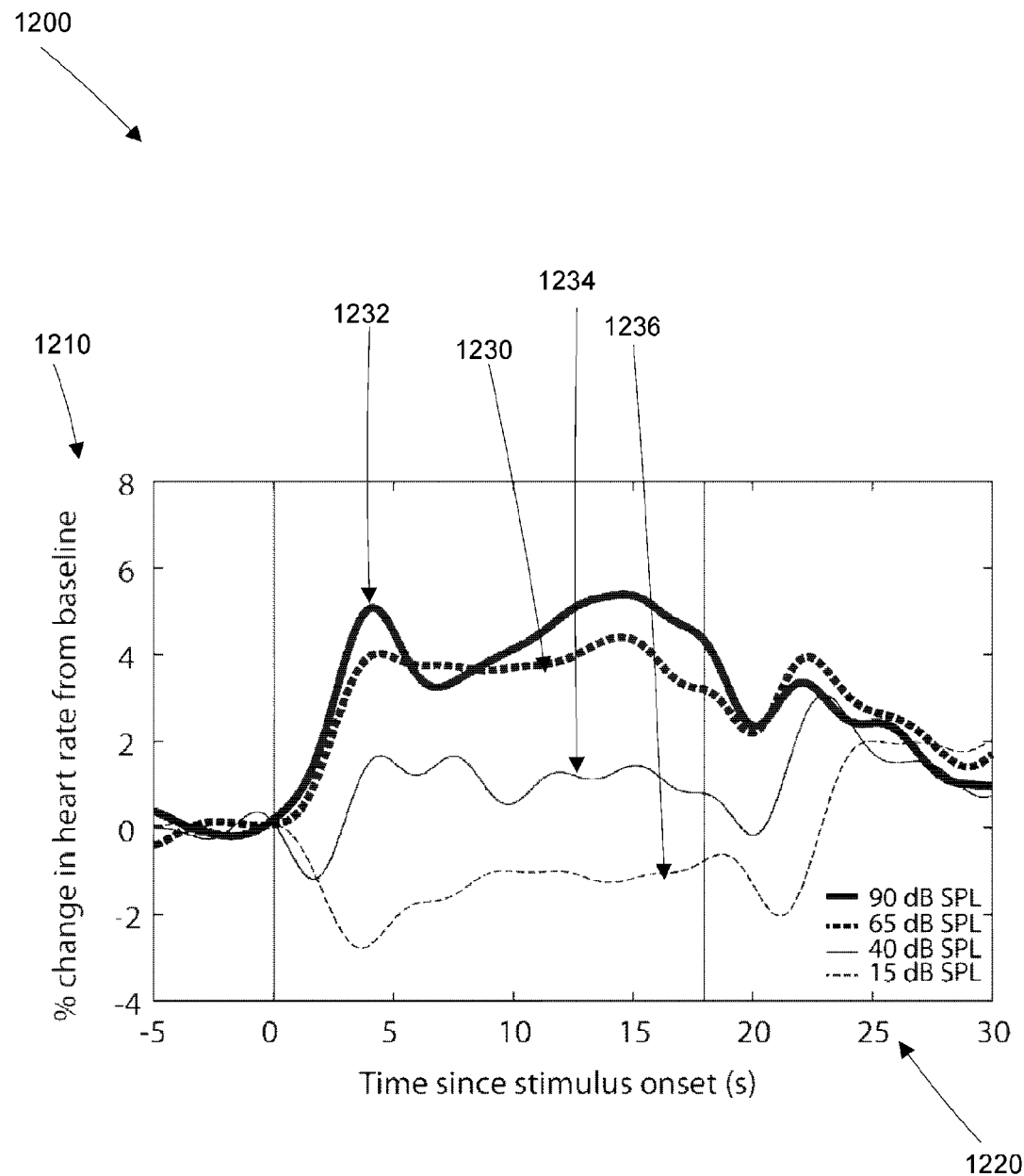
FIG. 12 shows an example graph of a measured percentage change in heart rate response to a plurality of aural stimulations.
Figure 18:
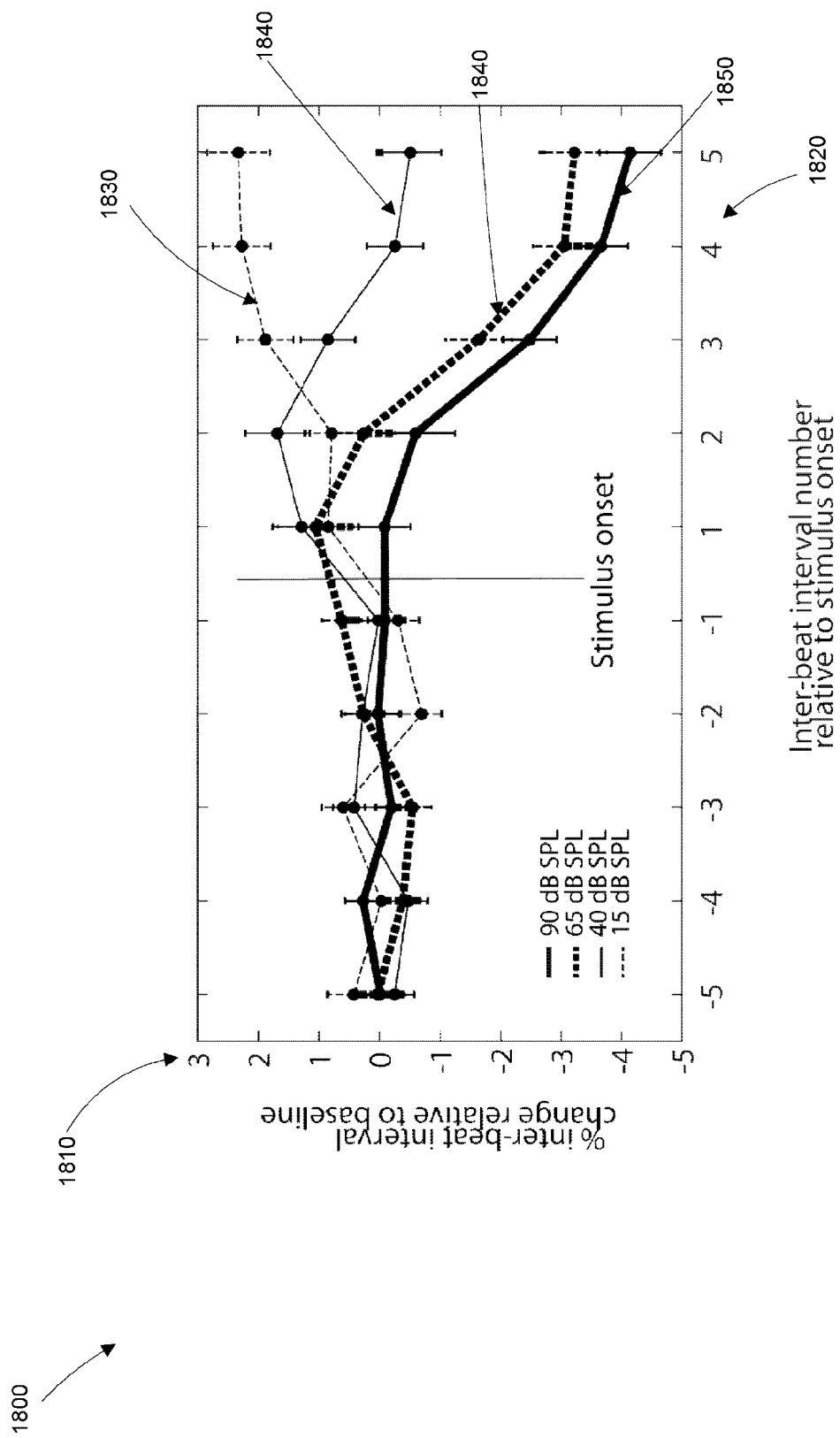
FIG. 18 shows an example graph illustrating a percentage change in inter-beat intervals in response to a plurality of aural stimulations averaged across a group of participants.

After pre-processing, processor 120 may execute automatic processing module 156, at step 614, to process the response signals relating to the change of HbO and HbR and/or the cardiac signals, if any. This may cause processor 120 to analyse the shape of the response signal 510, as illustrated in FIG. 5, and how response signal 510 varies over time, to extract predetermined parameters from the data, and associate these with the parameters of the stimulation signal, as determined and stored at step 602. Processor 120 may also analyse the shape of any extracted cardiac response signal data, such as signal 1230 as illustrated in FIG. 12 and FIG. 18. Parameters such as peak magnitude 501, width 502, time-to-peak 503, inter-peak intervals, and other features of the shape of response signal 510 and/or 1230 may be compared to predetermined ranges of values that may indicate whether the patient heard the stimulation, or whether the stimulation was of an uncomfortably high level, for example. Other measurements that may be associated with the stimulus parameters include the time taken to reach the peak magnitude after the stimulus onset, the duration of the response, and the difference in relative response magnitudes measured in different regions, which may be measured either at fixed times after the stimulus onset or at the peak response magnitude. The functional connectivity between different regions of the brain may also be measured.

In some embodiments, automatic processing module 156 may cause processor 120 to perform mathematical analysis of response signal 510/1230 and any other extracted signals, such as by performing statistical tests on the extracted signals in the temporal and frequency domains. In some embodiments, automatic processing module 156 may compare response signals from different areas of the patient's brain, to determine functional connectivity between the brain regions using correlation techniques. Automatic processing module 156 may also compare response signals from different brain regions with the cardiac response signals.

In some embodiments, only a single stimulation signal might be generated, in which case the process moves through step 616 to step 620, at which point the results of the data processing may be displayed on display 114. In some embodiments, the results may also be stored in memory 150 and/or communicated to external processing device 195 for further processing, viewing or storing.

In some other embodiments, further stimulation may be required to collect further data, at which stage the method may continue through to step 618. At step 618, processor 120 may execute sound generation module 195 to adjust the parameters of the stimulation signal. In some cases, the results of automatic processing at step 614 may be used to adjust the parameters of the subsequent stimulation signal. In some embodiments, these steps may be part of an automatic threshold seeking process, used to determine a patient's hearing range. In some embodiments, these steps may be part of an automatic process used to determine the limit of sound levels above which a patient considers the sound to be too loud.

In some embodiments, performing the automatic threshold seeking process may include adjusting the stimulation signal at step 618 to play a range of levels of sounds, mixing amplitudes and frequencies in a random or pseudo-random way, as further described with reference to FIGS. 9 and 19. The order of presentation of different sound intensities and the range and number of intensities presented can vary according to the particular application. A fixed range of levels and level step size can be determined from already-existing information if available. For example, if a hearing aid validation is required, and sounds are presented acoustically via the hearing aid, then the sounds should cover the input dynamic range of the hearing aid, which may include at least one sound expected to be below an aided hearing threshold in some embodiments.

Alternatively, an adaptive procedure can be undertaken, in which the level of the next sound is chosen based on the parameters derived from the response data evoked by the previous sound. This procedure may be used when programming the threshold and comfortable level currents in a cochlear implant patient, for example. The parameters of stimulation may be adjusted at step 618 in an incremental way, increasing and decreasing the parameters in turn until the targeted response parameter values are attained, which may be when the patient no longer exhibits a response to the stimulation being provided, for example. To find the sound level that corresponds to hearing threshold, the sound may be started at a low intensity and increased in pre-defined steps until a statistically significant response is determined in a least one parameter. The sound intensity may then be decreased in smaller steps, to find the lowest sound intensity that satisfies the pre-determined criterion for hearing threshold.

Other adaptive procedures to determine hearing threshold or comfortably loud levels could use a statistical procedure that estimates the likely level-versus loudness function and chooses the next level to test based on optimising the information to be gained. Examples of such procedures include the QUEST+ procedure, as described at http://jov.arvojournals.org/article.aspx?articleid=2611972, and the QUEST procedure, as described at https://link.springer.com/article/10.3758/BF03202828.

In some embodiments, performing the automatic process for determining uncomfortably loud sounds may include incrementally adjusting the stimulation signal at step 618, and waiting for peak magnitude 501 of response signal 510 to reach a threshold value that is known to correlate to uncomfortably loud sounds. According to some embodiments, an uncomfortable level of sound may be defined as a sound that evokes a strong response in either one or both of heart rate and anterior response, for example a peak response magnitude of $1 \times 10$-7 HbO concentration change relative to baseline, approximately, from optodes 162/164 in the anterior area, or a significant increase in heart rate (more than 3% increase, approximately). According to some embodiments, a comfortable-level sound may be defined as a sound that is the lowest level of intensity to evoke a positive response in HbO in the anterior regions, such as regions 811, 812, 815 and 816. According to some embodiments, a comfortable sound may be defined as a sound that is the lowest level of intensity to evoke an increase in heart rate.

Statistical methods such as Taylor's change-point analysis, statistical classification via machine learning, fuzzy logic, or other known techniques may be used to process the response signals and determine hearing thresholds or comfortable loudness or uncomfortable loudness. According to some embodiments, using more than one response signal to determine the signal loudness may be more reliable, as it may reduce the influence of noise on the result.

Once the parameters of the stimulation signal are appropriately adjusted at step 618, the method may move back to step 602.

Figure 14:
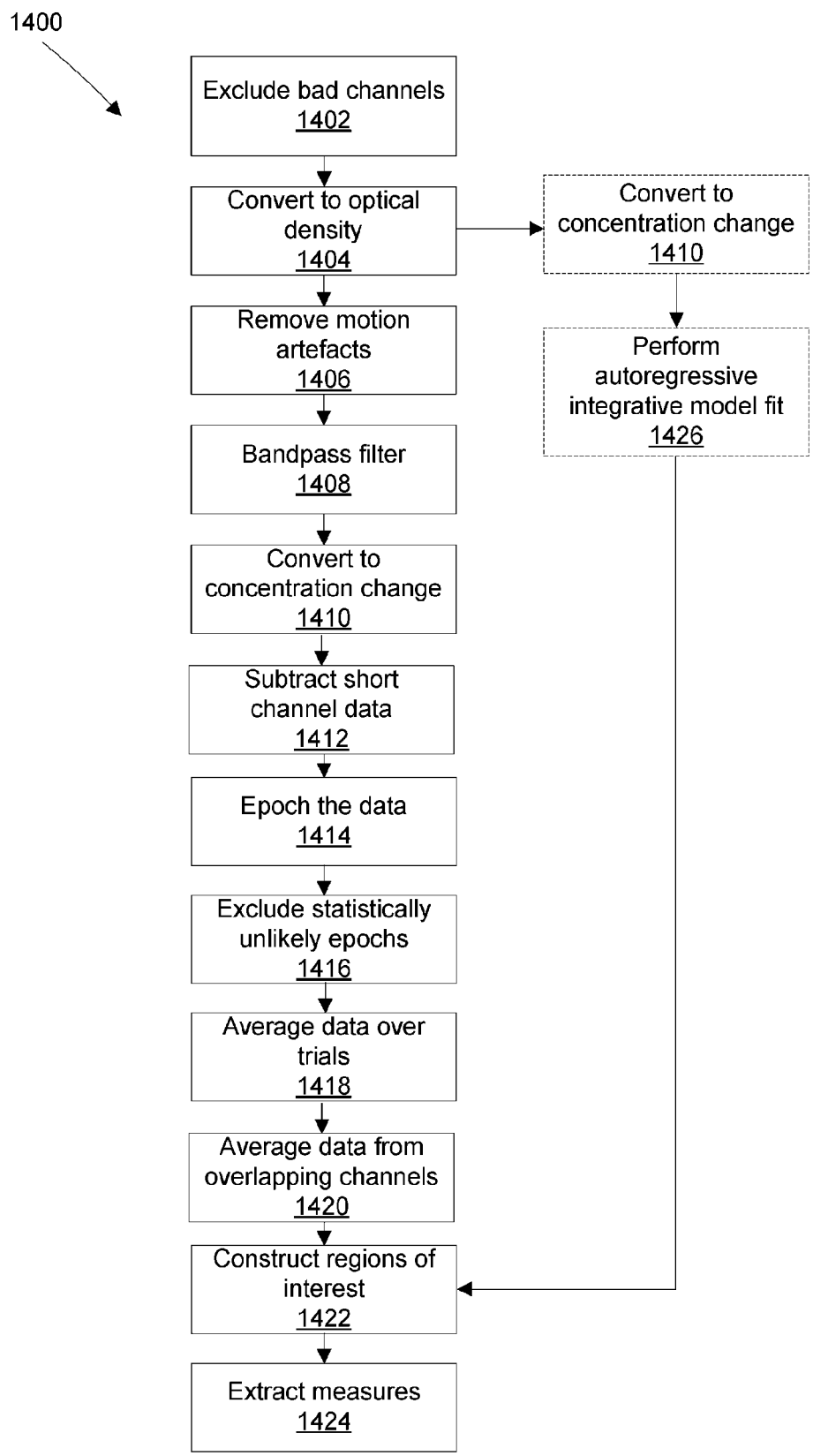
FIG. 14 shows a flow diagram illustrating an example pre-processing method using the system of FIG. 1.

FIG. 14 shows a flow diagram 1400 illustrating a method of pre-processing fNIRS data retrieved using system 100. At step 1402, channels 810 of data are excluded from further analysis if they are considered to be bad channels. According to some embodiments, bad channels may be the result of channels 810 in which the scalp of the patient and the optodes 162/164 are not well coupled. The identification and removal of bad channels may be done in a number of ways.

According to some embodiments, channels 810 with high gains may be considered bad channels and excluded from analysis, as high gains may correspond to low light intensity received by detector optodes 164. For example, if the connection between a detector optode 164 and the scalp of a patient is blocked by hair, or if the optode 164 is otherwise not in good contact with the skin, then the light received by detector optode 164 will have a relatively low intensity. Device 110 may be configured to automatically increase the gain for detector 164 where the signal being generated by detector 164 is low in magnitude. If this gain value is too high, this may indicate that there is poor coupling between detector 164 and the scalp, and that the data from that detector 164 should be discarded. Based on this, according to some embodiments step 1402 may include discarding channel values where the gain for the channel 810 is above a predetermined threshold value. Similarly if the automatically-set gain is very low, it may indicate that the source optode 162 may not be correctly placed against the scalp, and needs to be repositioned or the channel discarded. According to some embodiments, channels with gains over 7 may be discarded, as this may indicate inadequate scalp-electrode connection. According to some embodiments, channels with a gain under a predetermined threshold, or equal to a predetermined threshold, may also be discarded. For example, according to some embodiments, channels with a gain of 0 may be discarded.

According to some embodiments, channels with low correlation between the first wavelength and the second wavelength may also be considered bad channels and discarded, as described in Pollonini, L., Olds, C., Abaya, H., Bortfeld, H., Beauchamp, M. S., & Oghalai, J. S. (2014), "Auditory cortex activation to natural speech and simulated cochlear implant speech measured with functional near-infrared spectroscopy", *Hearing research*, 309, 84-93. Low correlation between the first wavelength and the second wavelength may be another indication of poor coupling between a detector 164 and the scalp of the patient. Data may first be filtered using a narrow bandpass filter, which may be used to filter out all signals apart from those in the heartbeat range, which may be signals between 0.5-1.5 Hz, or between 0.5 Hz and 2.5 Hz, for example. The remaining signal is dominated by the heartbeat signal, and is commonly the strongest signal in the raw fNIRS data received from detectors 164, and therefore should show up strongly in the signals for both the first wavelength and the second wavelength if both source 162 and detector 164 are well-coupled with the skin of the patient.

If the first wavelength and the second wavelength are strongly correlated, this indicates that the coupling between the scalp and detector 164 is sufficiently strong. If the coupling is poor, then the channel 810 may be excluded. Poor coupling may be defined as a case where the correlation coefficient less than 0.75, for example. Based on this, according to some embodiments step 1402 may include discarding channel values where the correlation coefficient between the HbO wavelength and the HbR wavelength signals is below a predetermined threshold value.

According to some embodiments, the correlation between the first and the second wavelength may be determined to be the scalp coupling index (SCI). The SCI may be calculated as the correlation between the two detected signals at the first wavelength and at the second wavelength, and filtered to a range that would mainly include heart beat data, as described above. For example, the SCI may be calculated as the correlation between the two detected signals at 760 and 850 nm and band-pass filtered between 0.5 and 2.5 Hz, in some embodiments. According to some embodiments, channels with SCIs lower than a predetermined threshold may be rejected. For example, according to some embodiments, channels with an SCI of less than 0.8 may be rejected. According to some embodiments, channels with an SCI of less than 0.75 may be rejected. According to some embodiments, channels with an SCI of less than 0.7 may be rejected.

At step 1404, the first wavelength raw data and the second wavelength raw data of the remaining channels are converted into a unit-less measure of changes in optical density over time. This step may be performed as described in Huppert, T. J., Diamond, S. G., Franceschini, M. A., & Boas, D. A. (2009), "HomER: a review of time-series analysis methods for near-infrared spectroscopy of the brain", *Appl Opt*, 48(10), D280-298. At step 1406, motion artefacts in the optical density data may be removed. According to some embodiments, motion artefacts may manifest as spike-shaped artefacts in the data. Motion artefacts may be removed using wavelets, as described in Molavi, B., & Dumont, G. A. (2012), "Wavelet-based motion artefact removal for functional near-infrared spectroscopy", *Physiological measurement*, 33(2), 259. In some embodiments, motion artefacts may be removed using threshold-crossing detection and spline-interpolation.

According to some embodiments, motion artefacts may also or alternatively be removed using techniques such as outlier detection using analysis of studentised residuals, use of principal component analysis (PCA) to remove signals with high covariance across multiple source-detector pairs and across optical wavelengths, Wiener filtering and autoregression models, as described in Huppert, T. J., Diamond, S. G., Franceschini, M. A., & Boas, D. A. (2009), "HomER: a review of time-series analysis methods for near-infrared spectroscopy of the brain", *Appl Opt*, 48(10), D280-298.

At step 1408, the signals generated at step 1406 may be passed through a bandpass filter to remove drift, broadband noise and/or systemic physiological responses such as heartbeat, respiration rhythm, systemic blood pressure and low frequency waves known as Mayer waves. According to some embodiments, the bandpass filter may be a 0.01 to 0.5 Hz bandpass filter. According to some embodiments, step 1408 may also or alternatively involve the removal of physiological signals in other ways, such as using other filtering methods, adaptive filtering or remote measurement of the signals to subtract them, as described in Kamran, M. A., Mannan, M. M. N., & Jeong, M. Y. (2016), "Cortical Signal Analysis and Advances in Functional Near-Infrared Spectroscopy Signal: A Review", Front Hum Neurosci, 10, and Huppert, T. J., Diamond, S. G., Franceschini, M. A., & Boas, D. A. (2009) "HomER: a review of time-series analysis methods for near-infrared spectroscopy of the brain", *Appl Opt*, 48(10), D280-298.

At step 1410, the signals generated at step 1408 may be converted to HbO and HbR concentration change signals, using the modified Beer-Lambert law as described in Delpy, D. T., Cope, M., van der Zee, P., Arridge, S., Wray, S., &

Wyatt, J. (1988), "Estimation of optical pathlength through tissue from direct time of flight measurement", Physics in medicine and biology, 33(12), 1433. Step 1410 may involve converting the optical density data as derived from the signals received from optodes 164 to concentration change units, taking into account the channel length, being the distance between the source 162 and the detector 164 optodes.

At step 1412, in order to remove the contribution of skin and scalp signals from the long channels, short channel data may be removed from the long channel data, either directly or by using a general linear model (GLM). In general, the shorter the distance between an optode pair 162/164, the shallower the area from which the signal is recorded. Therefore, very short channels measure activity only from the blood vessels in the skin and scalp. Very short channels may comprise source and detector pairs positioned around 1.5 cm or less apart. The skin and scalp signals may include signals relating to heartbeat, breathing and blood pressure.

According to some embodiments, principle component analysis (PCA) may be carried out across the short channels only. The first principle component (PC) across the short channels may represent activity common to all the short channels, which can then be included as a term in the general linear model of the long channel data and then effectively removed. According to some embodiments, this step may be carried out based on the methods outlined in Sato, T., Nambu, I., Takeda, K., Aihara, T., Yamashita, O., Isogaya, Y., . . . Osu, R. (2016), "Reduction of global interference of scalp-hemodynamics in functional near-infrared spectroscopy using short distance probes", *NeuroImage,* 141, 120-132.

At step 1414, the time series of HbO and HbR concentration change data determined at step 1412 may be epoched. Each epoch may be from around −5 to 30 seconds relative to the onset time of the stimulus. According to some embodiments, the stimulus may be 18 seconds long, leaving 12 seconds after the stimulus finishes for the signal to return to baseline. According to some embodiments, other epoch time values may be used depending on stimulus length and silent period length.

At step 1416, epochs with statistically unlikely concentration change values may be excluded. For example, epochs with early stimulation phase values within the range of mean plus 2.5 standard deviations (across trials) may be included, and all other epochs may be excluded. The early stimulation phase may be defined as from −5 to +2 seconds in some embodiments. According to some embodiments, step 1416 may be performed as described in Huppert, T. J., Diamond, S. G., Franceschini, M. A., & Boas, D. A. (2009), "HomER: a review of time-series analysis methods for near-infrared spectroscopy of the brain", *Appl Opt,* 48(10), D280-298. The excluded epochs may relate to movement artefacts and noise.

At step 1418, where multiple different stimuli have been presented during the measurements, data resulting from each of the stimulations may be separately averaged. At step 1420, where overlapping channels 810 of optodes 162/164 were used, the averaged responses from the overlapping channels may be averaged. Averaging data across overlapping channels may reduce noise in the data.

At step 1422, regions of interest (ROIs) may be constructed based on the positions of the optodes 162/164, as described above with reference to FIG. 8. According to some embodiments, two or more neighbouring channels may be combined into one ROI. Channels to group as ROIs may be selected according to similar response waveform patterns, for example. Channels to group as ROIs may be also be selected according to pre-determined anatomical or functional considerations In an alternative embodiment, after step 1404, step 1410 is performed. At step 1410, the signals generated at step 1404 may be converted to HbO and HbR concentration change signals, using the modified Beer-Lambert law as described in Delpy, D. T., Cope, M., van der Zee, P., Arridge, S., Wray, S., & Wyatt, J. (1988), "Estimation of optical pathlength through tissue from direct time of flight measurement", Physics in medicine and biology, 33(12), 1433. Step 1410 may involve converting the optical density data as derived from the signals received from optodes 164 to concentration change units, taking into account the channel length, being the distance between the source 162 and the detector 164 optodes. The method may then proceed to step 1426, during which the response signal may be modelled using either an autoregressive integrative model fit of the data as described in Barker et al. 2013, or a real-time implementation of an adaptive general linear model as described in Abdelnour et al. 2009. After step 1426, the method may proceed to step 1422.

At step 1424, measures may be automatically extracted from the response signals. These measures may include a calculated magnitude of the peak of the signal, if the response shows single peak, or a calculated mean magnitude in an early and/or late window of the signal. According to some embodiments, an early window may be a window of around 3 to 9 seconds from the stimulation onset time, and a late window may be a window of around 14 to 20 seconds from the stimulation onset time. According to some embodiments, the response magnitude may be averaged over multiple time windows of various durations and centre times covering all or part of the epoched time window. According to some embodiments, an early window may be a window of around 0 to 6 seconds from the stimulation onset time, and a late window may be a window of around 24 to 30 seconds from the stimulation onset time. According to some embodiments, the measures may also or alternatively include a calculated time to the peak of the signal, and/or a width of the peak of the signal. According to some embodiments, the measures may include values associated with modelling the response signal using an autoregressive integrative (ARI) model fit of the data as described in Barker et al. 2013, or a real-time implementation of an adaptive general linear model as described in Abdelnour et al. 2009. In some embodiments, the measures may the beta-value obtained from modelling the response signal using a general linear model.

Figure 15:
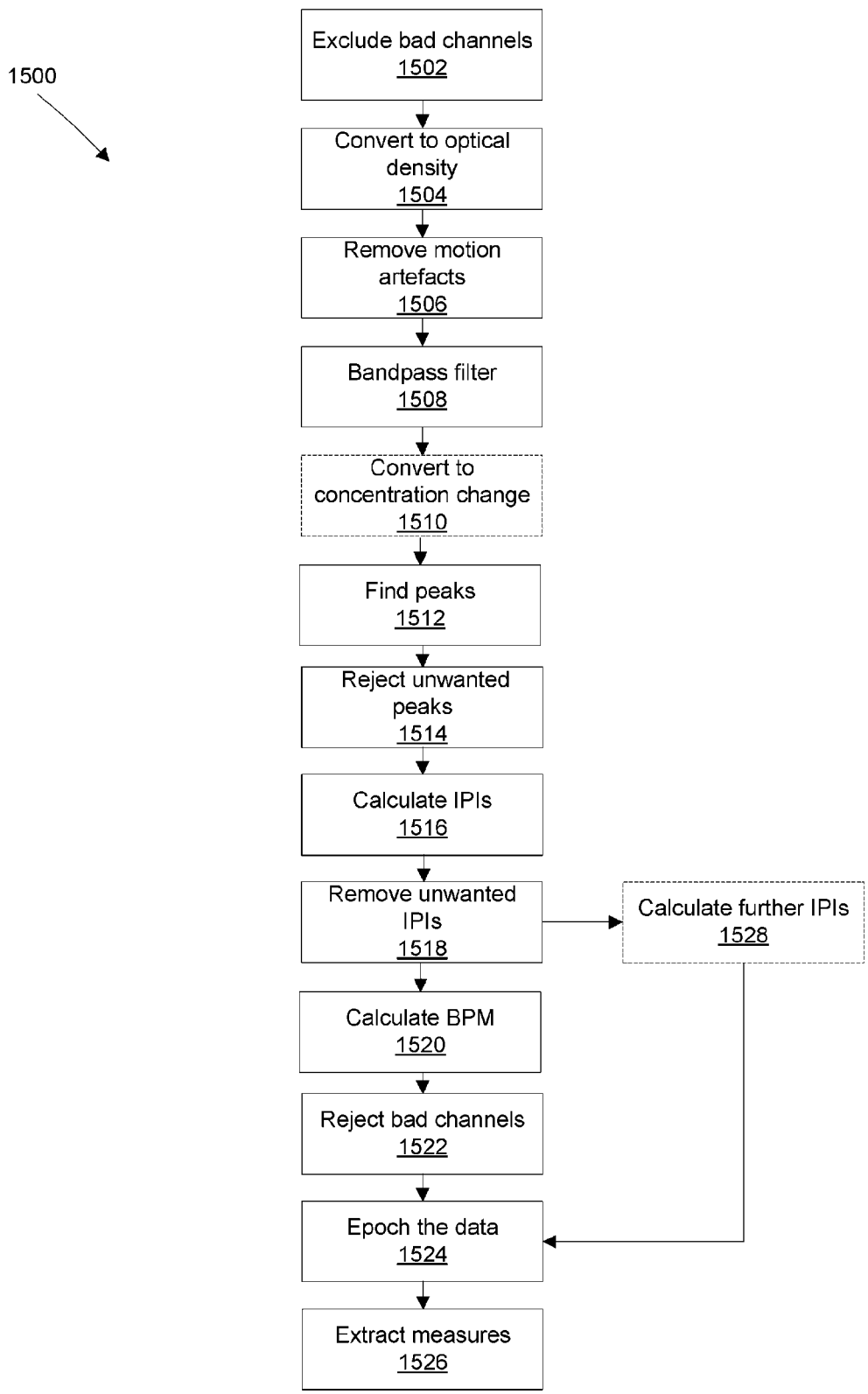
FIG. 15 shows a flow diagram illustrating an alternative example method using the system of FIG. 1.

FIG. 15 shows a flow diagram 1500 illustrating a method of determining cardiac data from fNIRS data generated by channels 810 of system 100. As described below with reference to FIG. 12, cardiac data may be used to assess hearing of a patient. Cardiac signals may be used in conjunction with or independent of HbO and HbR data to perform a hearing assessment. Cardiac signals may be determined using fNIRS as described here with reference to FIG. 15, or may alternatively or in addition be generated by cardiac monitor 165.

At step 1502, after channels 810 have been used to generate fNIRS data, bad channels of data are excluded from further analysis. According to some embodiments, bad channels may be the result of channels in which the scalp of the patient and the optodes 162/164 are not well coupled. The identification and removal of bad channels may be done in a number of ways.

According to some embodiments, channels with high gains may be considered to be bad channels and may be excluded from analysis, as high gains may correspond to low light intensity received by detector optodes 164. For example, if the connection between a detector optode 164 and the scalp of a patient is blocked by hair, then the light received by detector optode 164 will have a relatively low intensity. Device 110 may be configured to automatically increase the gain for a detector 164 if the detector 164 detects a low intensity of light. If this gain value is too high, this may indicate that there is poor coupling between detector 164 and the scalp, and that the data from that detector 164 should be discarded. Based on this, according to some embodiments step 1402 may include discarding channel values where the gain for the channel is above a predetermined threshold value. Similarly if the automatically-set gain is very low, it may indicate that the source optode may not be correctly placed against the scalp, and needs to be repositioned or the channel discarded. According to some embodiments, channels with gains over 7 may be discarded, as this may indicate inadequate scalp-electrode connection. According to some embodiments, channels with a gain under a predetermined threshold may also be discarded. For example, according to some embodiments, channels with a gain of 0 may be discarded.

According to some embodiments, channels with low correlation between the first wavelength and the second wavelength may also be considered to be bad channels and be discarded, as described in Pollonini, L., Olds, C., Abaya, H., Bortfeld, H., Beauchamp, M. S., & Oghalai, J. S. (2014), "Auditory cortex activation to natural speech and simulated cochlear implant speech measured with functional near-infrared spectroscopy", *Hearing research*, 309, 84-93. Low correlation between the first wavelength and the second wavelength may be another indication of poor coupling between a detector 164 and the scalp of the patient. Data may first be filtered using a narrow bandpass filter, which may be used to filter out all signals apart from those in the heartbeat range, which may be signals between 0.5-1.5 Hz, or between 0.5 and 2.5 Hz, for example. The remaining signal is dominated by the heartbeat signal, and is commonly the strongest signal in the raw fNIRS data received from detectors 164, and therefore should show up strongly in the signals for both the first wavelength and the second wavelength if both source 162 and detector 164 are well-coupled with the skin of the patient.

If the first wavelength and the second wavelength are strongly correlated, this indicates that the coupling between the scalp and detector 164 is sufficiently strong. If the coupling is poor, then the channel may be excluded. Poor coupling may be defined as a case where the correlation coefficient less than 0.75, for example. Based on this, according to some embodiments step 1402 may include discarding channel values where the correlation coefficient between the HbO wavelength and the HbR wavelength signals is below a predetermined threshold value.

According to some embodiments, the correlation between the first and the second wavelength may be determined to be the scalp coupling index (SCI). The SCI may be calculated as the correlation between the two detected signals at the first wavelength and at the second wavelength, and filtered to a range that would mainly include heart beat data, as described above. For example, the SCI may be calculated as the correlation between the two detected signals at 760 and 850 nm and band-pass filtered between 0.5 and 2.5 Hz, in some embodiments. According to some embodiments, channels with SCIs lower than a predetermined threshold may be rejected. For example, according to some embodiments, channels with an SCI of less than 0.8 may be rejected. According to some embodiments, channels with an SCI of less than 0.75 may be rejected. According to some embodiments, channels with an SCI of less than 0.7 may be rejected.

At step 1504, the remaining channels of first wavelength raw data and the second wavelength raw data are converted into a unit-less measure of changes in optical density over time. This step may be performed as described in Huppert, T. J., Diamond, S. G., Franceschini, M. A., & Boas, D. A. (2009), "HomER: a review of time-series analysis methods for near-infrared spectroscopy of the brain", *Appl Opt*, 48(10), D280-298.

At step 1506, motion artefacts in the optical density data signals may be removed. According to some embodiments, motion artefacts may manifest as spike-shaped artefacts in the fNIRS data. Motion artefacts may be removed using wavelet analysis, as described in Molavi, B., & Dumont, G. A. (2012), "Wavelet-based motion artifact removal for functional near-infrared spectroscopy", *Physiological measurement*, 33(2), 259. In some embodiments, motion artefacts may be removed using threshold-crossing detection and spline-interpolation.

According to some embodiments, motion artefacts may also or alternatively be removed using techniques such as outlier detection using analysis of studentised residuals, use of principal component analysis (PCA) to remove signals with high covariance across multiple source-detector pairs and across optical wavelengths, Wiener filtering and autoregression models, as described in Huppert, T. J., Diamond, S. G., Franceschini, M. A., & Boas, D. A. (2009), "HomER: a review of time-series analysis methods for near-infrared spectroscopy of the brain", *Appl Opt*, 48(10), D280-298.

At step 1508, the signals generated at step 1506 may be passed through a bandpass filter to obtain only the part of the signal dominated by the heartbeat signal. According to some embodiments, filtering the signals may remove drift, broadband noise and unwanted physiological responses. According to some embodiments, the bandpass filter may be a 0.5 to 1.5 Hz bandpass filter. According to some embodiments, the bandpass filter may be determined for each person based on their pre-determined approximate average resting heart rate. According to some embodiments, step 1508 may also or alternatively involve the removal of unwanted signals in other ways, such as using other filtering methods, adaptive filtering or remote measurement of the signals to subtract them, as described in Kamran, M. A., Mannan, M. M. N., & Jeong, M. Y. (2016), "Cortical Signal Analysis and Advances in Functional Near-Infrared Spectroscopy Signal: A Review", Front Hum Neurosci, 10, and Huppert, T. J., Diamond, S. G., Franceschini, M. A., & Boas, D. A. (2009) "HomER: a review of time-series analysis methods for near-infrared spectroscopy of the brain", *Appl Opt*, 48(10), D280-298.

Optionally, at step 1510, the signals generated at step 1508 may be converted to HbO and HbR concentration change, using the modified Beer-Lambert law as described in Delpy, D. T., Cope, M., van der Zee, P., Arridge, S., Wray, S., & Wyatt, J. (1988), "Estimation of optical pathlength through tissue from direct time of flight measurement", *Physics in medicine and biology*, 33(12), 1433. Step 1510 may involve converting the unit-less optical density data as derived from the signals received from optodes 164 to concentration change units, taking into account the channel length, being the distance between a paired source optode 162 and detector optode 164. According to some embodiments, step 1510 may be excluded, and method step 1512 may be performed on the filtered signal derived at step 1508.

At step 1512, the signal determined at step 1508 or 1510 is up-sampled to around 100 Hz, as outlined in Perdue, K. L., Westerlund, A., McCormick, S. A., & Nelson, C. A., 3rd. (2014), "Extraction of heart rate from functional near-infrared spectroscopy in infants", *J Biomed Opt*, 19(6), 067010. The up-sampled signal may then be used to find peaks in the data, which may correspond to heart beats.

At step 1514, unwanted peaks determined at step 1512 are rejected. Peaks may be rejected from the data if the width of the peak is determined to be larger than the mean+1.5 standard deviations of mean widths. Peaks that are too wide may be a result of noise rather than heartbeats, and should therefore be removed from the signal data. According to some embodiments, peaks may also be rejected if the time between peaks is too small, or below a predetermined threshold.

At step 1516, the times between the peaks that were not rejected at step 1512 are calculated. The time between peaks may be known as the inter-peak interval, or IPI.

At step 1518, unwanted IPIs may be rejected. Unwanted IPIs may be IPIs greater than the mean plus 2 standard deviations across all determined IPIs, in some embodiments. According to some embodiments, IPIs bigger or smaller than a predetermined threshold may also be deleted.

At step 1520, beats per minute (BPM) of the remaining IPIs is calculated, by finding the inverse of the IPIs and multiplying by 60. This results in a time series of beats per minute versus time. However, at this point the time has non-uniform steps, as it corresponds to time points where peaks were detected in the signal. In order to get uniform time intervals for later averaging across epochs, the signal is then resampled to 20 Hz. The signal may also be passed through a low-pass filter to remove abrupt changes in heart beat rate which are likely not physiological in origin. Step 1520 may be performed as described in Perdue, K. L., Westerlund, A., McCormick, S. A., & Nelson, C. A., 3rd. (2014), "Extraction of heart rate from functional near-infrared spectroscopy in infants", *J Biomed Opt*, 19(6), 067010.

In an alternative embodiment, step 1518 is followed by step 1528. At step 1528, IPIs for a predetermined number of beats before and after stimulation onset may be recorded. For example, as described in further detail below with reference to FIG. 18, IPIs for 5 heart beats before and 5 heart beats after stimulation onset may be recorded. From step 1528, the method may proceed to step 1526.

At step 1522, the average and the standard deviation of the heart rate versus time as determined at step 1520 is calculated across all channels 810. If a channel 810 has values outside predetermined thresholds, the channel 810 may be rejected. According to some embodiments, channels 810 with values outside a range of mean heart rate plus/minus 20 beats/min are rejected. According to some embodiments, channels 810 with values outside a range mean heart rate plus/minus a predetermined number of standard deviations are rejected. According to some embodiments, channels with IPIs outside of the range of mean IPI plus-or-minus a predetermined number of standard deviations are rejected. According to some embodiments, the calculations in step 1522 may be performed on a single channel 810. According to some embodiments, the calculations in step 1522 may be averaged over a group of channels 810 chosen to have low noise.

At step 1524, the data determined at step 1520 or step 1528 may be epoched. Each epoch may be from around −5 to 30 seconds relative to the onset time of the stimulus. According to some embodiments, other time values may also be used according to stimulus length and length of silent periods. In cases where multiple different stimuli have been applied in different epochs, epochs may be averaged based on the stimulus identity, to result in one average for each separate stimulus. This results in data according to the graph shown in FIG. 12.

At step 1526, measures may be automatically extracted from the data determined at step 1524. These measures may include a percentage change in heart rate compared to average heart rate in the 5 seconds before stimulus onset, being the baseline heartrate; the peak change in heart rate from the baseline; the time to reach the peak from the onset time; and other parameters such as the width of the peak. These measures may be used to determine hearing thresholds or comfortable loudness or uncomfortable loudness, as described above with reference to FIG. 6.

FIGS. 10A, 10B, 11A and 11B show graphs 1000, 1050, 1100 and 1150, respectively, illustrating an example set of changes of HbO in response to an audio stimulus in regions 811 and 814 (as illustrated in FIG. 8).

Figure 10A:
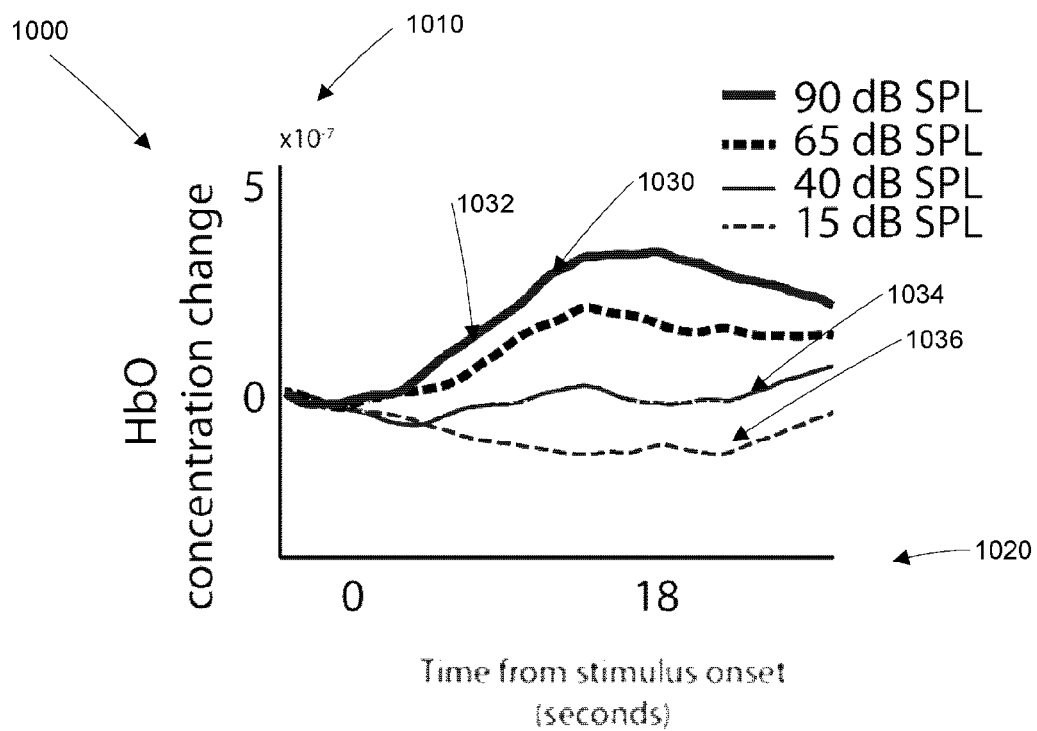
FIG. 10A shows an example graph of a measured response in one region of the brain to an aural stimulation over time.
Figure 10B:
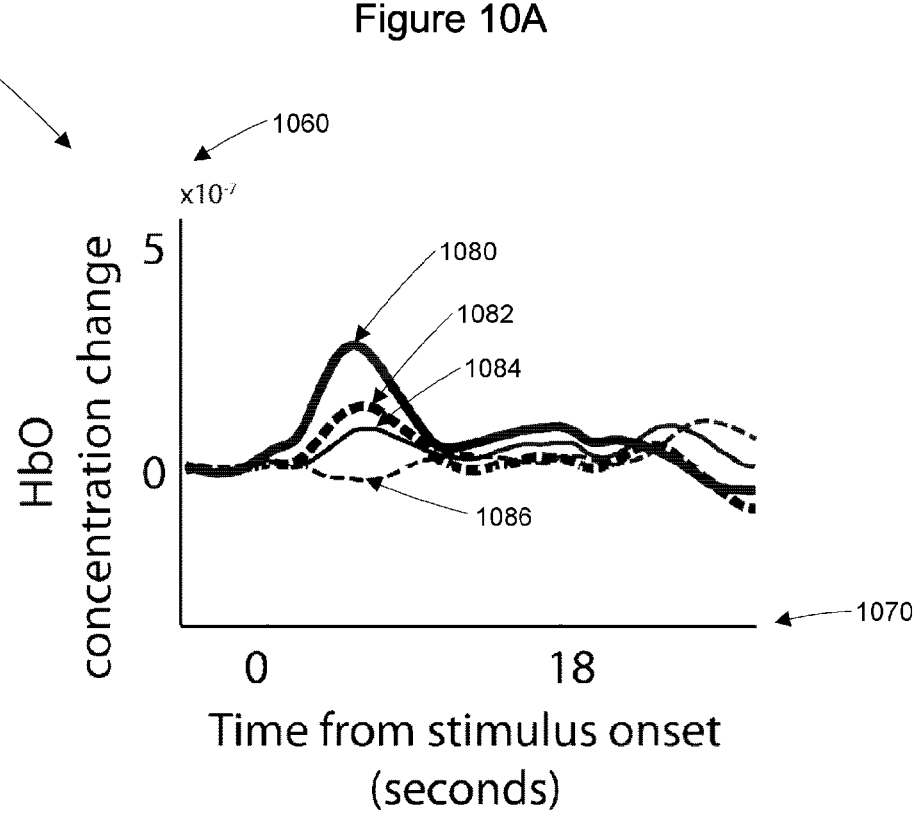
FIG. 10B shows an example graph of a measured response in a second region of the brain to an aural stimulation.

In graphs 1000 and 1050, shown in FIGS. 10A and 10B, x-axes 1020 and 1070 define the time from the stimulus onset in seconds, where the stimulus begins at 0 seconds. Y-axes 1010 and 1060 define the HbO concentration change, where 0 is the average concentration of HbO while no sound stimulus is being delivered. Responses 1030 and 1080 relate to a stimulus of 90 dB sound pressure level (SPL), responses 1032 and 1082 relate to a stimulus of 65 dB SPL, responses 1034 and 1084 relate to a stimulus of 40 dB SPL and responses 1036 and 1086 relate to a stimulus of 15 dB SPL. Graph 1000 illustrates the rate of change of HbO in region 811, while graph 1050 shows the rate of change of HbO in region 814.

Figure 11A:
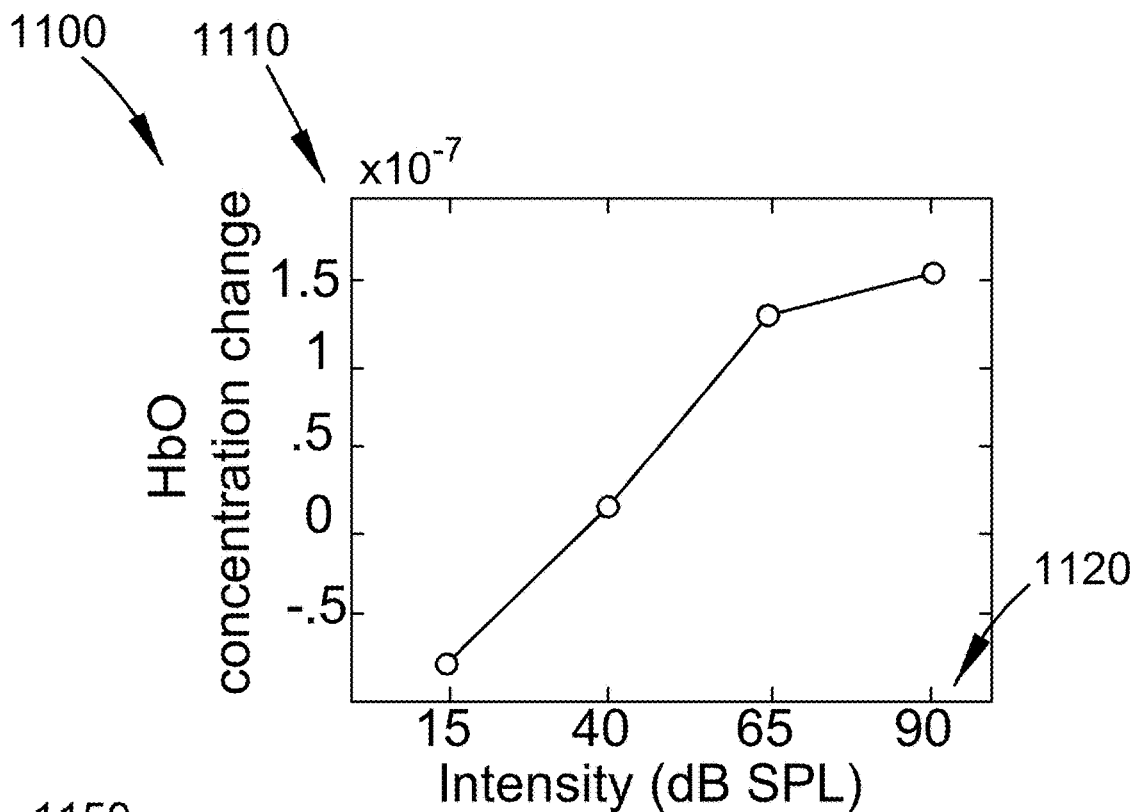
FIG. 11A shows an example graph of measured peak responses in one region of the brain to a plurality of aural stimulations.
Figure 11B:
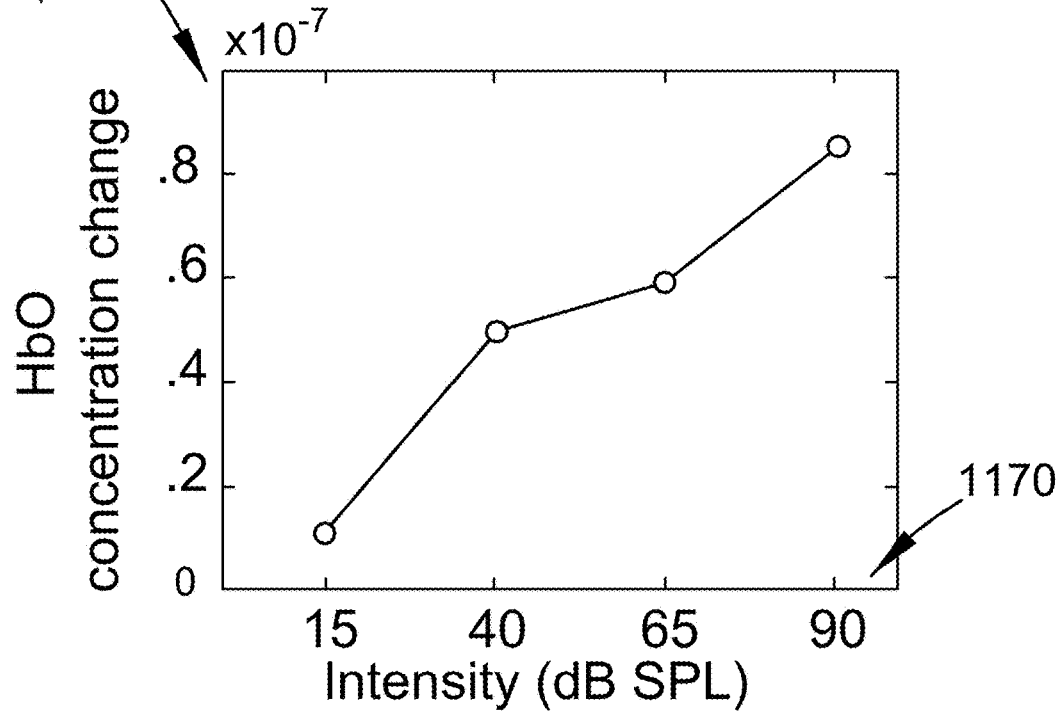
FIG. 11B shows an example graph of measured peak responses in a second region of the brain to a plurality of aural stimulations.

In graphs 1100 and 1150, shown in FIGS. 11A and 11B, x-axes 1120 and 1170 define the intensity in dB SPL of an audio stimulation delivered to a patient. Y-axes 1110 and 1160 define the HbO concentration change, where 0 is the concentration of HbO while no sound stimulus is being delivered. Graph 1100 illustrates the response amplitude of HbO in region 811, and the amplitude of HbO concentration change was calculated as a mean amplitude in a time window extending 24 to 30 seconds after the onset of the audio stimulation. Graph 1150 shows the response amplitude of HbO in region 814, and the amplitude of HbO concentration change was calculated as a mean amplitude in a time window extending 0 to 6 seconds after the onset of audio stimulation.

FIG. 12 shows a graph 1200 illustrating an example set of changes of heart rate in response to an audio stimulus, with the heart rate having been calculated by fNIRS, as described above with reference to step 612 of method 600 and method 1500. According to some embodiments, changes in heart rate may also be determined based on data generated by cardiac monitor 165. X-axis 1220 defines the time from the stimulus onset in seconds, where the stimulus begins at 0 seconds. Y-axis 1210 defines the percentage change in heart rate from the heart rate when there is no stimulation, being a baseline heart rate. In the illustrated example, the baseline heart rate was around 70 beats per minute. Response 1230 relates to a stimulus of 90 dB SPL, response 1232 relates to a stimulus of 65 dB SPL, response 1234 relates to a stimulus of 40 dB SPL and response 1236 relates to a stimulus of 15 dB SPL. For responses 1234 and 1236, an initial drop and subsequent rise in heart rate can be seen following the stimulus onset at 0 seconds. Response 1236 shows an average drop in heart rate of 4% over 4.6 seconds after stimulus onset, and response 1234 shows an average drop in heart rate of 1.1% over 1.6 seconds after stimulus onset. Responses 1232 and 1230 show heart rate increasing following stimulus onset, with both responses reaching similar average levels.

It can be seen from FIG. 12 that a soft sound of 15 dB SPL induces a slight reduction in heart rate early after the stimulus onset. The reduction in heart rate for a 15 dB SPL sound may be up to around 3%. In contrast, a loud sound of around 90 dB induces a strong increase in heart rate that persists while the stimulus is on. The increase in heart rate for a 90 dB SPL sound may be up to around 10%.

Figure 16:
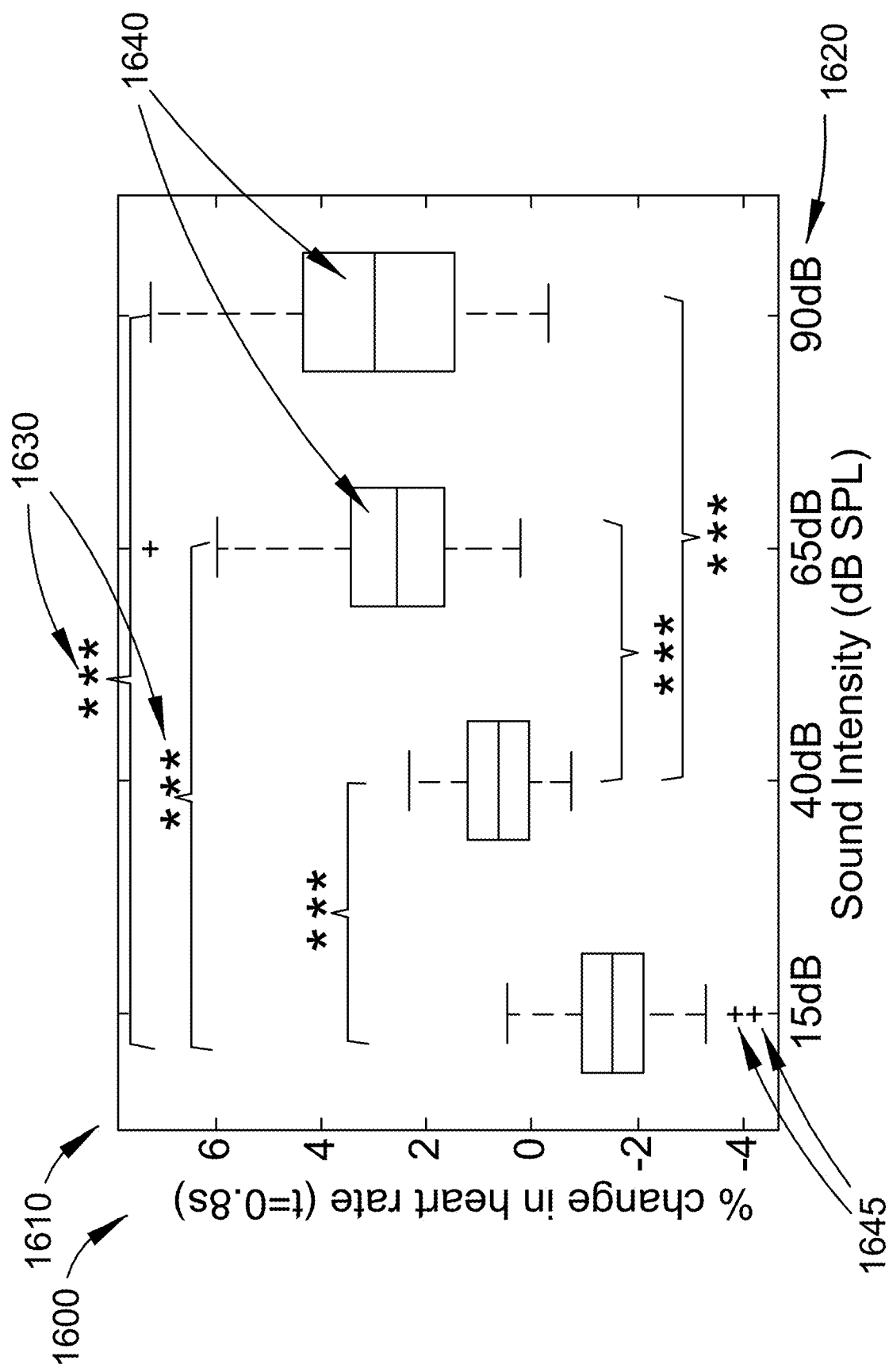
FIG. 16 shows an example graph illustrating a percentage change in heart rate in response to a plurality of aural stimulations averaged across a group of participants.

To quantify the immediate change in responses 1230, 1232, 1234 and 1236 after stimulus onset, the mean heart rate change between 0 seconds and 8 seconds may also be calculated, and the results of an example of such a calculation are shown in FIG. 16.

FIG. 16 shows a graph 1600 having a y-axis 1210 showing the percentage change in heart rate of the recorded signal of FIG. 12 for a predetermined post-stimulation period, and an x-axis 1620 showing the level of sound intensity of the stimulation in dB SPL. In the illustrated embodiment, the post-stimulation period is between 0 and 8 seconds after the stimulation onset. An 8 second period was be chosen to cover the initial peak seen after stimulation onset in the averaged data as shown in FIG. 12, but a different period may be chosen in some embodiments.

Pairings 1630 show comparisons between intensity levels where a significant effect on heart rate change was found, with a significant effect defined as p<0.001. As illustrated, a significant effect of intensity level on heart rate change was found in pairwise comparisons 1630 showing significant difference between all sound intensity levels except at 65 dB and 90 dB. At the higher stimulus levels of 65 and 90 dB, a bi-phasic response with peaks at 4 and 14.5 seconds post-stimulus onset can be seen in FIG. 12.

As seen in FIG. 12, at stimulus offset, an initial decrease in heart rate at all stimulation intensity levels was observed, following which the heart rate at all stimulus intensity levels returned to the baseline measurement.

Boxes 1640 represent the median, interquartile range and largest/smallest non-outliers from a sample of 27 tested patients. Crosses 1645 represent outliers, defined as values greater than 1.5 times the interquartile range.

Figure 17:
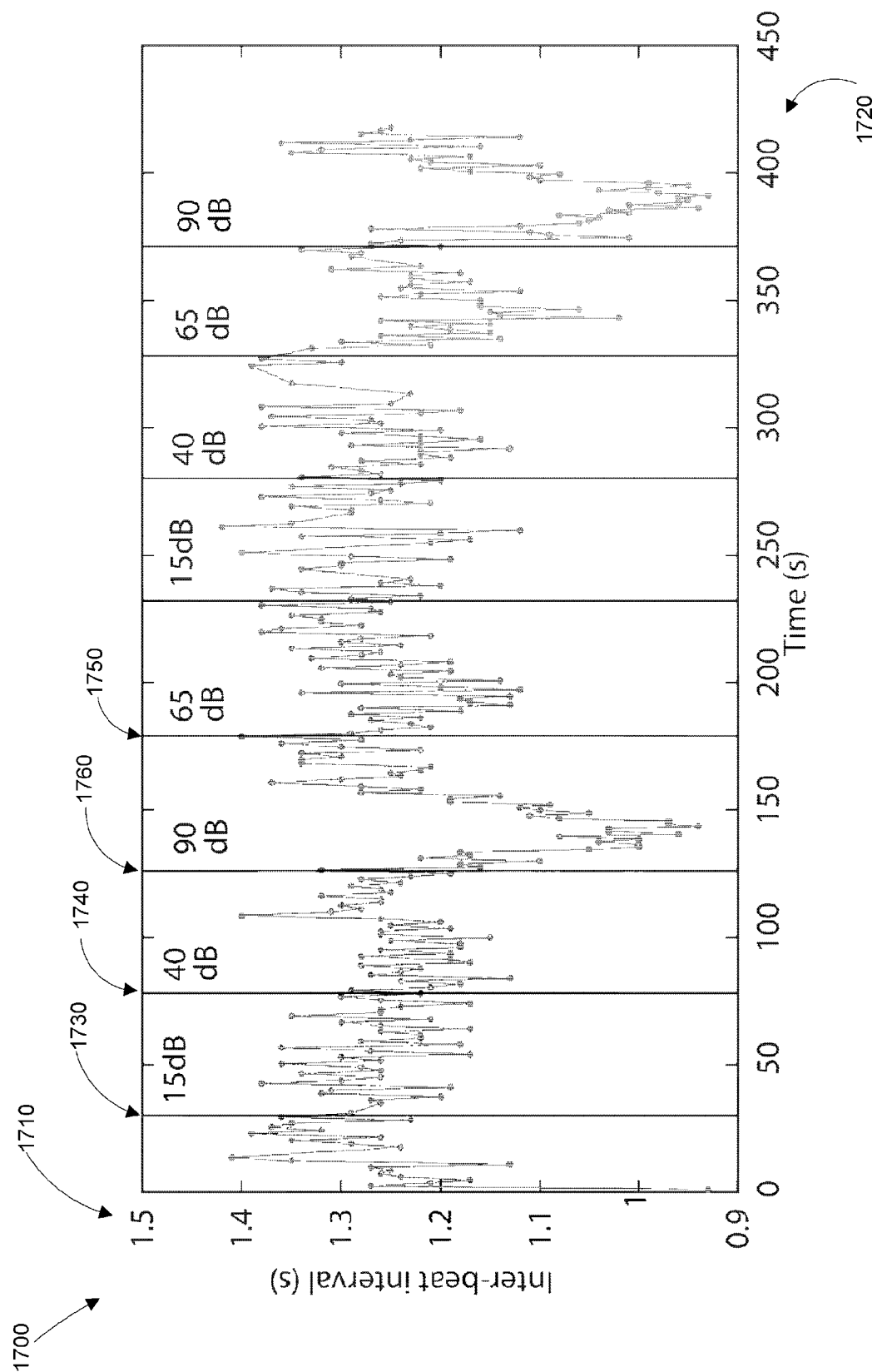
FIG. 17 shows an example graph illustrating a change in inter-beat intervals in response to a plurality of aural stimulations in one participant.

FIG. 17 shows a graph 1700 with a y-axis 1710 showing inter-beat intervals (or time between heart beats) in seconds for one example patient during a seven minute recording with stimulus levels of 15 dB, 40 dB, 60 dB and 90 dB presented in a random order. The x-axis 1720 shows time in seconds. Lines 1730 correspond to a stimulus of 15 dB being delivered, lines 1740 correspond to a stimulus of 40 dB being delivered, lines 1750 correspond to a stimulus of 65 dB being delivered, and lines 1760 correspond to a stimulus of 90 dB being delivered.

A drop in inter-beat intervals (corresponding to an increased heart rate) following the 65 and 90 dB SPL levels at lines 1750 and 1760 are clearly seen. To illustrate the immediate change in inter-beat intervals following sound onset in more detail, the percentage change in the first five intervals after sound onset relative to baseline (defined as the averaged five intervals before stimulus onset), may be calculated. An example of this calculation is shown in FIG. 18, described in further detail below.

FIG. 18 shows a graph 1800 having a y-axis 1810 showing the percentage of inter-beat interval change relative to a baseline measurement for inter-beat intervals, and an x-axis 1820 showing the inter beat interval number relative to the stimulus onset. Graph 1800 shows inter-beat intervals staring from 5 intervals before the stimulus onset, up to 5 intervals after the stimulus onset. Four sets of data are shown. Data 1 is shown by line 1830 and corresponds to a stimulus of 15 dB. Data 2 is shown by line 1840 and corresponds to a stimulus of 40 dB. Data 3 is shown by line 1850 and corresponds to a stimulus of 65 dB. Data 4 is shown by line 1860 and corresponds to a stimulus of 90 dB.

Table 1 below shows the percentage change in inter-beat intervals averaged across the first two intervals and also across intervals three to five. For both these ranges, a significant stimulus level x time interaction was found (P<0.001) indicating changes in intervals after stimulus onset were dependent on stimulus levels.

TABLE 1

Mean (SEM) percentage change in inter-beat intervals from baseline, across participants.

| Stimulus level (dB SPL) | Mean (SEM) inter-beat intervals 1 to 2 (%) | P value (change from baseline) | Mean (SEM) inter-beat intervals 3 to 5 (%) | P value (change from baseline) |
|---|---|---|---|---|
| 15 | 0.82 (0.41) | 0.529 | 2.17 (0.37) | <0.001*** |
| 40 | 1.48 (0.41) | 0.011* | 0.03 (0.37) | 1.0 |
| 65 | 0.66 (0.43) | 0.779 | −2.63 (0.40) | <0.001*** |
| 90 | −0.34 (0.45) | 0.993 | −3.43 (0.34) | <0.001*** |

*P < 0.05,
***P < 0.001

Post-hoc comparison shows that across the first two beats, the average change from the baseline measurement was only significant in data 1840, being the 40 dB SPL beat. At this sound level, after the first two inter-beat intervals, values returned toward baseline and were not significantly different from baseline when averaged across intervals three to five (see FIG. 18). Averaged inter-beat intervals three to five were significantly higher than baseline at 15 dB SPL as shown by data 1830, and significantly lower at stimulus levels 65 and 90 dB SPL, as shown by data 1850 and data 1860. Following stimulus onset, the change in inter-beat intervals three to five from baseline was significantly different between all stimulus levels except 65 and 90 dB SPL. Similar responses to those shown in FIGS. 12 and 16 to 18 may be determined for breathing rate, blood pressure, and other cardiac responses. These response signals may be used alone or in combination with neural activity responses to determine threshold levels of hearing for the patient or loudness of above-threshold sounds. According to some embodiments, the hearing threshold values for a patient may be obtained by fitting a function to the values at different sound intensities and interpolating or extrapolating a parameter value designated as corresponding to threshold.

Figure 13:
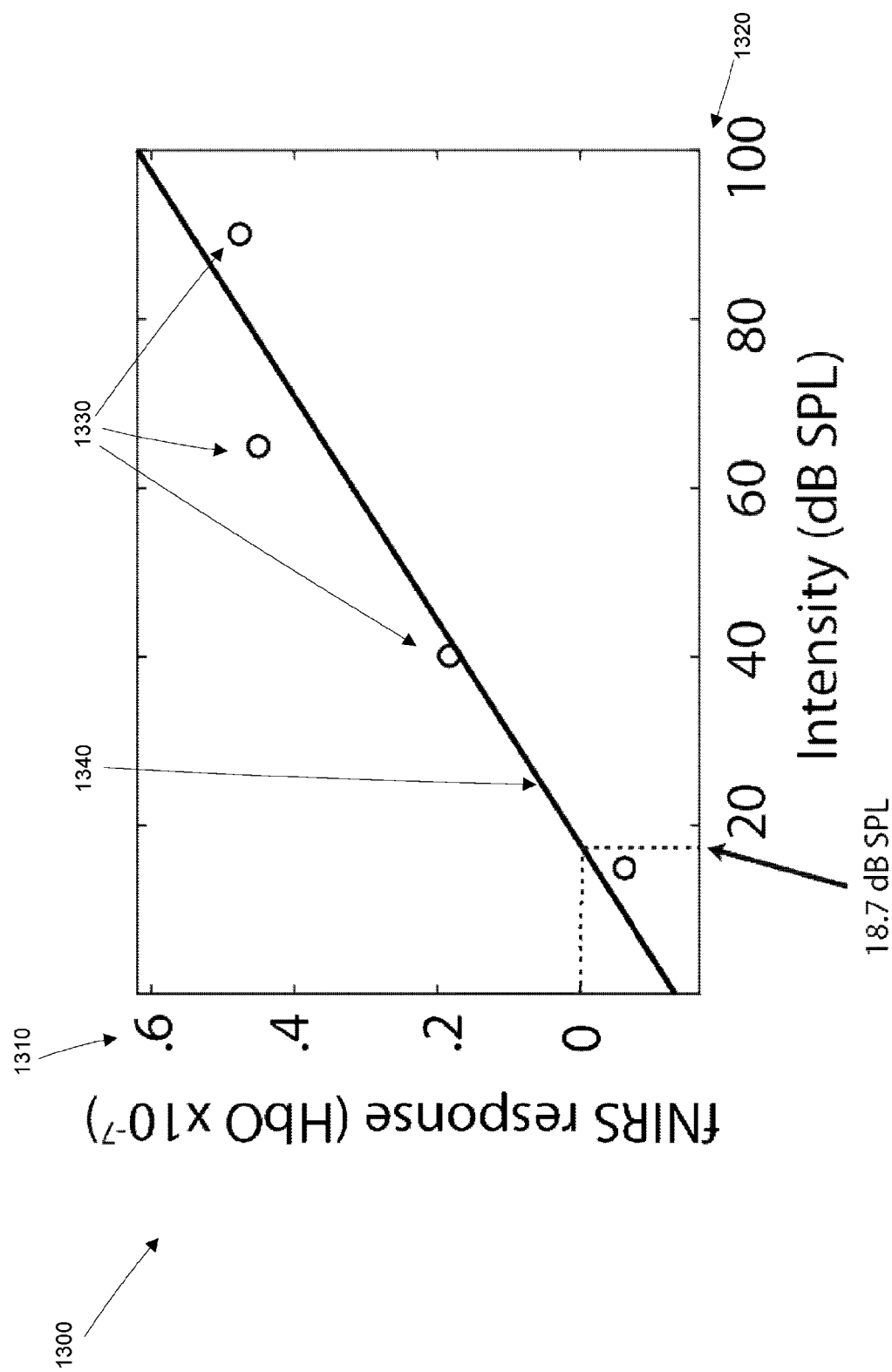
FIG. 13 shows an example graph of measured responses in a region of the brain to a plurality of aural stimulations extrapolated to zero.

FIG. 13 shows a graph 1300 having an x-axis 1320 of intensity in dB SPL and a y-axis 1310 of fNIRS response in HbO change. Graph 1300 illustrates a number of data points 1330, being the peak magnitude of the response in a patient as measured in region 814. Line 1340 shows the magnitude of the response in region 814 is extrapolated to zero. The sound intensity at which this occurs is the fNIRS-estimated threshold. In the illustrated embodiment, this is around 18 dB SPL. Using a 3-alternative forced-choice adaptive procedure, the behaviourally-determined threshold for detecting the sound was determined to be 12.5 dB SPL in this patient.

Alternatively, the hearing threshold for a patient may be determined as the lowest sound intensity that satisfies one or more parameter values. For example, in the scenario illustrated by FIGS. 10A to 11B, the hearing threshold may be determined as the lowest sound intensity for which region 811 shows a suppression or a negative response, or in the scenario illustrated by FIG. 12, the lowest sound intensity for which the heart rate decreases after stimulus onset, or a combination of these and other parameters.

Figure 19:
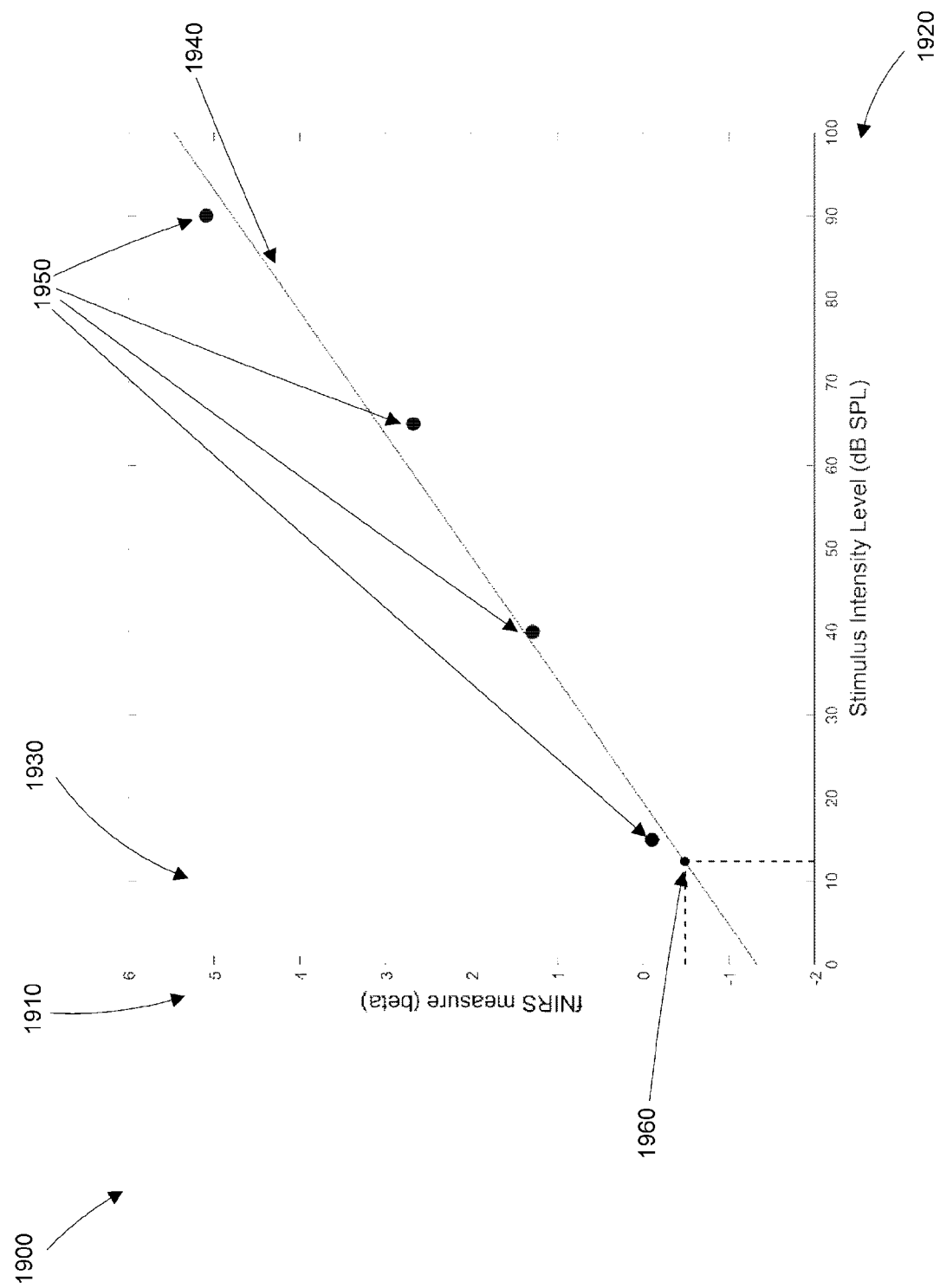
FIG. 19 shows an example graph illustrating a change in beta values with stimulation level for one participant, showing how hearing threshold can be determined from such a graph.

FIG. 19 shows a graph 1900 having an x-axis 1920 of intensity in dB SPL and a y-axis 1910 of a beta value fNIRS measure. Graph 1900 illustrates a number of data points 1950, being the beta values of the fNIRS response in a patient. Line 1940 shows the magnitude of the response is extrapolated to zero dBSPL. The sound intensity at which line 1940 reaches the beta value measured in the rest period is the fNIRS-estimated threshold. In the illustrated embodiment, this is around 12.4 dB SPL, as indicated by point 1960 and the dotted lines. Using a 3-alternative forced-choice adaptive procedure, the behaviourally-determined threshold for detecting the sound was determined to be 10 dB SPL in this patient, as illustrated by line 1930.

Alternatively, the hearing threshold for a patient may be determined as the lowest sound intensity that satisfies one or more parameter values. For example, in the scenario illustrated by FIGS. 10A to 11B, the hearing threshold may be determined as the lowest sound intensity for which region 811 shows a suppression or a negative response, or an increase or positive response, or in the scenario illustrated by FIG. 12, the lowest sound intensity for which the heart rate decreases after stimulus onset, or a combination of these and other parameters.

According to some embodiments, the system and methods described above can be used in combination with simultaneously-collected EEG measures of electrical brain responses to auditory stimulation, using standard methods such as ABR (auditory brainstem response) CAEP (Cortical auditory evoked potentials) ASSR (auditory steady-state responses). The simultaneous use of multi-dimensional data that includes both fNIRS and/or cardiac data along with EEG data may optimise the accuracy and/or reliability of the estimates of the clinical parameters of threshold and comfortable loudness levels.

According to some embodiments, the methods described above may be used in combination with other objective measures of hearing, such as EEG, physiological responses such as skin conductance, respiration rate, blood pressure changes, and with any available behavioural measures or observations.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method of assessing the hearing of a patient using functional near-infrared spectroscopy (fNIRS), the method comprising:
    determining parameters of aural stimulation to be delivered to the patient, the parameters including a first intensity;
    delivering to the patient the aural stimulation having the first intensity;
    receiving at least one response signal from an optode placed on a scalp of the patient, the at least one response signal comprising fNIRS data generated by the optode and relating to the aural stimulation received by the patient;
    comparing at least one parameter of the at least one response signal to a predetermined parameter value;
    estimating, based on the result of the comparison and to assess the hearing of the patient, a loudness perceived by the patient experiencing the aural stimulation;
    determining new parameters of aural stimulation to be delivered to the patient, the new parameters including a second intensity that is different from the first intensity;
    delivering to the patient further aural stimulation having the second intensity; and
    repeating the steps of receiving at least one response signal from an optode, comparing at least one parameter of the at least one response signal to a predetermined parameter value, and estimating a loudness perceived by the patient experiencing the aural stimulation.

2. The method of claim 1, wherein the at least one response signal comprises signals relating to at least one of brain activity of the patient and cardiac activity of the patient.

3. The method of claim 1, further comprising processing the at least one response signal to remove at least one unwanted signal element.

4. The method of claim 3, wherein the at least one unwanted signal element comprises a signal element associated with at least one of the breathing of the patient, the heartbeat of the patient, a Mayer wave, a motion artefact, the brain activity of the patient, and measurement noise generated by a data collection apparatus.

5. The method of claim 1, wherein the at least one parameter includes at least one of:
    a peak magnitude of the response signal;
    a width of the response signal;
    a lag time of a peak magnitude of the response signal compared to the time at which the aural stimulation was received by the patient; and
    a value associated with modelling the response signal using at least one of an autoregressive integrative model fit of the data and a real-time implementation of an adaptive general linear model.

6. The method of claim 1, wherein the predetermined parameter value corresponds to a parameter of the aural stimulation received by the patient.

7. The method of claim 1, wherein the receiving at least one response signal comprises receiving a plurality of response signals, the method further comprising excluding any received response signals that are determined to be bad signals, wherein estimating the loudness perceived by determining the patient comprises estimating the loudness based on at least one parameter derived from the remaining response signals.

8. The method of claim 7, wherein bad signals include at least one of:
    signals that indicate poor coupling between the optode and the scalp;
    signals with a gain higher than a predetermined threshold;
    signals with a gain lower than a predetermined threshold;
    signals with a gain equal to a predetermined threshold; and
    signals with a scalp coupling index lower than a predetermined threshold.

9. The method of claim 1, further comprising filtering the at least one response signal.

10. The method of claim 9, wherein the filtering is performed using at least one of a low-pass filter, a high-pass filter or a band-pass filter.

11. The method of claim 1, wherein the receiving at least one response signal comprises receiving at least one signal from a first optode configured to measure brain activity of the patient and receiving at least one signal from a second optode configured to measure at least one signal that is not related to brain activity; the method further comprising producing a processed signal by removing at least one signal received from the second optode from at least one signal received from the first optode, to retain only information relating to brain activity from the at least one signal received from the first optode; wherein the estimating the loudness perceived by the patient comprises estimating the loudness based on at least one parameter derived from the processed signal.

12. The method of claim 1, wherein the parameters of the aural stimulation are determined based on a measured auditory response signal based on previously delivered aural stimulation.

13. A device for assessing the hearing of a patient using functional near-infrared spectroscopy (fNIRS), the device comprising:
   a processor;
   at least one data input channel;
   wherein the processor is configured to perform the method of claim 1, and wherein the response signal is received by the processor from the at least one data input channel.

14. The device of claim 13, further comprising at least one of memory accessible to the processor and a sound generation module to generate the aural stimulation received by the patient.

15. A system for assessing the hearing of a patient using fNIRS, the system comprising:
   the device of claim 13; and
   a stimulation member to deliver the aural stimulation to the patient.

16. The system of claim 15, further comprising at least one source optode to emit NIR light, and at least one detector optode to measure light intensity and communicate data to the data input channel of the device corresponding to the light intensity.

17. The system of claim 16, wherein the system comprises headgear configured to be worn by the patient and the at least one source optode and the at least one detector optode are affixed to the headgear.

18. The system of claim 17, wherein the source optodes and detector optodes are affixed to the headgear in a configuration such that when the headgear is correctly worn by the patient, the at least one source optode and the at least one detector optode are situated in the region of the temporal lobe of the patient.

19. The system of claim 15, further comprising a cardiac monitor configured to measure at least one form of cardiac data of the patient and to communicate data to the data input channel of the device.

20. The system of claim 19, wherein the cardiac data comprises at least one of respiratory data, heartbeat data, and blood pressure data.

21. The system of claim 15, wherein the stimulation member comprises two stimulation delivery components configured to provide binaural stimulation.

22. The system of claim 15, further comprising electrodes configured to determine EEG measures of electrical responses of at least one of a cortex or brainstem of the patient in response to an auditory stimulus.

23. The method of claim 1, further comprising calculating a hearing range of the patient based on the estimated loudness perceived by the patient experiencing the aural stimulation at at least the first intensity and the second intensity.

24. The method of claim 1, wherein calculating the hearing range of the patient includes calculating at least one of an aural stimulus intensity corresponding to the intensity below which the patient cannot hear the aural stimulation, and an aural stimulus intensity corresponding to the intensity above which the sound is uncomfortably loud.

* * * * *